US008340745B2

(12) United States Patent
Balas

(10) Patent No.: US 8,340,745 B2
(45) Date of Patent: Dec. 25, 2012

(54) METHODS FOR CHARACTERIZING CANCER AND PRE-CANCER TISSUES

(75) Inventor: Constantinos Balas, Athens (GR)

(73) Assignee: Forth Photonics Ltd., London (GB)

( * ) Notice: Subject to any disclaimer, the term of this patent is extended or adjusted under 35 U.S.C. 154(b) by 883 days.

(21) Appl. No.: 11/810,699

(22) Filed: Jun. 5, 2007

(65) Prior Publication Data

US 2008/0039720 A1    Feb. 14, 2008

Related U.S. Application Data

(60) Provisional application No. 60/810,930, filed on Jun. 5, 2006.

(51) Int. Cl.
*A61B 6/00* (2006.01)

(52) U.S. Cl. .................... 600/476; 600/477

(58) Field of Classification Search .......... 600/473, 600/475, 476, 477; 436/164; 424/9.6; 530/409; 382/128

See application file for complete search history.

(56) References Cited

U.S. PATENT DOCUMENTS

2002/0007122 A1   1/2002   Kaufman et al.
2004/0073120 A1*  4/2004   Motz et al. ............ 600/478

FOREIGN PATENT DOCUMENTS

| WO | WO 01/72214 A1 | 10/2001 |
| WO | WO 03/077750 A1 | 9/2003 |
| WO | WO 2004/005885 A2 | 1/2004 |

OTHER PUBLICATIONS

C. Bales, "A Novel Optical Imaging Method for the Early Detection, Quantitative Grading, and Mapping of Cancerous and Precancerous Lesions of Cervix", IEEE Transactions of Biomedical Engineering, vol. 48, No. 1, Jan. 2001.*

(Continued)

*Primary Examiner* — Long V. Le
*Assistant Examiner* — Nicholas L Evoy
(74) *Attorney, Agent, or Firm* — Nixon & Vanderhye P.C.

(57) ABSTRACT

A quantitative method for determining tissue characteristics includes the steps of generating data for a dynamic optical curve over a period of time based on an optical property of a tissue, or portion thereof, that has been exposed to a biomarker and, based on the data, determining a value of a dynamic optical parameter. The value of the dynamic optical parameter is compared with at least one reference value of the dynamic optical parameter known to be linked to a structural or functional characteristic and/or the pathological status of the tissue. Based on the comparison, a structural or functional characteristic and/or the pathological status of the tissue, or portion thereof is determined. Data for dynamic optical curves may be generated for a plurality of tissue locations corresponding to a plurality of spatial image locations. The plurality of dynamic optical curves may be used to determine values of a dynamic optical parameter and a related tissue characteristic at a plurality of tissue locations. A computer readable medium holds computer program instructions for carrying out this method. Reference values can be calculated by measuring dynamic optical properties from known representative tissue samples. Preferred tissue samples include endothelial and cervical samples. Preferred methods involve diagnosing and/or grading neoplasia and/or HPV infection and/or calculating nuclear to cytoplasmic ratios of the cells in the tissue sample.

23 Claims, 11 Drawing Sheets

OTHER PUBLICATIONS

I.M. Stefanaki et al., "In vivo detection of human papilloma virus-induced lesions of anogenital area after application of acetic acid: a novel and accurate approach to a trivial method", Journal of Photochemistry and Photobiology B: Biology 65 (2001) 115-121.*

Orfanoudaki et al., "A Clinical Study of Optical Biopsy of the Uterine Cervix Using a Multispectral Imaging System," Gynecologic Oncology, vol. 96, 2005, pp. 119-131.

Balas et al., "In Vivo Detection and Staging of Epithelial Dysplasias and Malignancies Based on the Quantitative Assessment of Acetic Acid-Tissue Interaction Kinetics," Rapid Communication, J. Photochem, Photobiol. B: Biol., vol. 53, 1999, pp. 153-157.

Glanzmann et al., "Time-Resolved Spectrofluorometer for Clinical Tissue Characterization During Endoscopy," Review of Scientific Instruments, vol. 70, No. 10, Oct. 1999, pp. 4067-4077.

Andersson-Engels et al., "Preliminary Evaluation of Two Fluorescence Imaging Methods for the Detection and the Delineation of Basal Cell Carcinomas of the Skin," Lasers in Surgery and Medicine, vol. 26, 2000, pp. 76-82.

Notification of Transmittal of the International Search Report and the Written Opinion of the International Searching Authority, or the Declaration Mailed Jan. 21, 2008 in International Application No. PCT/GB2007/002067 (13 pages).

Notification Concerning Transmittal of International Preliminary Report on Patentability Mailed Dec. 24, 2008 in International Application No. PCT/GB2007/002067 (8 pages).

Examination Report Dated Mar. 18, 2009 in European Application No. 07 823 884.7 (4 pages).

Nanda et al., "Accuracy of the Papanicolaou Test in Screening For and Follow-Up of Cervical Cytologic Abnormalities: A Systematic Review," Annals of Internal Medicine, vol. 132, No. 10, May 16, 2000, pp. 810-819.

Sankaranarayanan et al., "A Critical Assessment of Screening Methods for Cervical Neoplasia," International Journal of Gynecology & Obstetrics, vol. 89, 2005, pp. S4-S12.

Mitchell et al., "Colposcopy for the Diagnosis of Squamous Intraepithelial Lesions: A Meta-Analysis," Obstetrics & Gynecology, vol. 91, No. 4, Apr. 1998, pp. 626-631.

Schiffman et al., "Findings to Date From the ASCUS-LSIL Triage Study (ALTS)," Arch Pathol Lab Med, vol. 127, Aug. 2003, pp. 946-949.

Cantor et al., "Cost-Effectiveness Analysis of Diagnosis and Management of Cervical Squamous Intraepithelial Lesions," Obstetrics & Gynecology, vol. 91, No. 2, Feb. 1998, pp. 270-277.

Ismail et al., "Observer Variation in Histopathological Diagnosis and Grading of Cervical Intraepithelial Neoplasia," British Medical Journal, vol. 298, Mar. 18, 1989, pp. 707-710.

Bellina et al., "Reliability of Histopathologic Diagnosis of Cervical Intraepithelial Neoplasia," Southern Medical Journal, vol. 75, No. 1, Jan. 1982, pp. 6-8.

Robertson et al., "Observer Variability in Histopathological Reporting of Cervical Biopsy Specimens," J Clin Pathol, vol. 42, 1989, pp. 231-238.

Walker et al., "A Study of the Morphological Parameters of Cervical Squamous Epithelium," Institute of Physics Publishing, Physiological Measurement, vol. 24, 2003, pp. 121-135.

Webb et al., "Mathematical Modelling of Tumour Acidity: Regulation of Intracellular pH," J. Theor. Biol., vol. 196, 1999, pp. 237-250.

Lee et al., "Heterogeneity of Intracellular pH and of Mechanisms That Regulate Intracellular pH in Populations of Cultured Cells," Cancer Research, vol. 58, May 1, 1998, pp. 1901-1908.

Yamagata et al., "The Chronic Administration of Drugs That Inhibit the Regulation of Intracellular pH: in vitro and anti-tumour effects," British Journal of Cancer, vol. 73, Nos. 7-12, Apr.-Jun. 1996, pp. 1328-1334.

Stubbs et al., "Causes and Consequences of Tumour Acidity and Implications for Treatment," Molecular Medicine Today, vol. 6, Jan. 2000, pp. 15-19.

Prescott et al., "The Relationship Between Intracellular and Extracellular pH in Spontaneous Canine Tumors," Clinical Cancer Research, vol. 6, Jun. 2000, pp. 2501-2505.

Maddox et al., "Differential Expression of Keratins 10, 17, and 19 in Normal Cervical Epithelium, Cervical Intraepithelial Neoplasia, and Cervical Carcinoma," J Clin Pathol, vol. 52, 1999, pp. 41-46.

Carrilho et al., "Keratins 8, 10, 13, and 17 Are Useful Markers in the Diagnosis of Human Cervix Carcinomas," Human Pathology, vol. 35, No. 5, May 2004, pp. 546-551.

Fahey et al., "Meta-Analysis of Pap Test Accuracy," American Journal of Epidemiology, vol. 141, No. 7, 1995, pp. 680-689.

Kohonen, "Self-Organization, Memorization, and Associative Recall of Sensory Information by Brain-Like Adaptive Networks," International Journal of Quantum Chemistry: Quantum Biology Symposium 13, 1986, pp. 209-221.

Loukas et al., "An Image Analysis-Based Approach for Automated Counting of Cancer Cell Nuclei in Tissue Sections," Cytometry Part A 55A, 2003, pp. 30-42.

MacLEAN, "Acetowhite Epithelium," Gynecologic Oncology, vol. 95, 2004, pp. 691-694.

Office Action of Oct. 3, 2011 issued in Russian Federation Appln. No. 2008152386, with English Translation (14 pages).

Wu et al., "Study of Dynamic Process of Acetic Acid Induced-Whitening in Epithelial Tissues at Cellular Level," Optics Express, vol. 13, No. 13, Jun. 27, 2005, pp. 4963-4973.

Sokolov et al., "Optical System for In Vivo Molecular Imaging of Cancer," Technology in Cancer Research & Treatment, ISSN 1533-0346, vol. 2, No. 6, Dec. 2003, pp. 491-504.

* cited by examiner

METHODS FOR CHARACTERIZING CANCER AND PRE-CANCER TISSUES

RELATED APPLICATIONS

This application claims priority to, and the benefit of U.S. Provisional Application No. 60/810,930, filed Jun. 5, 2006, the entire contents of which is hereby incorporated herein by reference.

FIELD OF THE INVENTION

Embodiments of the invention relate to automated and semi-automated diagnostic methods for in vivo screening, and for clinical diagnosis, respectively. In particular, the methods rely on the quantitative assessment of dynamic optical phenomena occurring in tissues after the application of specific biomarkers and on the determination of the predictive reference values of dynamic optical parameters.

BACKGROUND OF THE INVENTION

Currently, diagnostic and screen procedures are used to detect and grade epithelial cancers and pre-cancers for the purposes of diagnosis and treatment. In the case of the cervix of the uterus the development of screening programs for cancer prevention often targets the early detection and identification of its curable precursors such as Cervical Intraepithelial Neoplasia (CIN).

The Pap-test is the primary screening method for cervical neoplasia. During this test, a large number of cells are obtained from the cervical epithelium, and are cytologically examined after appropriate fixation and staining. The accuracy of this method is limited by both sampling and reading errors, leading to a significant false negative rate. A great number of studies have been performed aiming to determine the performance of the Pap-test over the past years. Researchers agree that the mean sensitivity is 0.59 and the mean specificity is 0.69-0.75 [Nanda K et al. (2000) *Annals of Internal Medicine*, 16; 132(10): 810-819; Sankaranarayanana R, et al. (2005) *International Journal of Gynecology and Obstetrics*, 89:S4-S12; and Fahey M T et al. (1995) *American Journal of Epidemiology*, 141: 680-689]. It is also widely accepted that the Pap-test is unable to achieve concurrently high specificity and sensitivity. For example, a possible increase of specificity in the 0.90-0.95 range will result in a decrease of sensitivity in the 0.20-0.35 range [Fahey M T et al. (1995) *American Journal of Epidemiology*, 141: 680-689].

Typically, sensitivity (SS) and specificity (SP) are used as quantitative statistical parameters to describe the performance of diagnostic tests. The sensitivity expresses the percentage of the True Positives (TP), while specificity expresses the percentage of the True Negatives (TN). For example, a sensitivity of 80% (or 0.80) means that the test diagnoses correctly 80 of the 100 cases diagnosed as positive for the disease, with the aid of the gold standard test (the most definitive test or procedure against which other tests are measured).

In a routine clinical setting, an abnormal Pap stained smear is followed by colposcopy, which involves examination of the cervix using a low power microscope. The cervical tissue is evaluated according to the following criteria: a) the morphology of the lesion's margins; b) the vascular pattern of abnormal epithelium; and c) the degree of staining after topical application of a marker, such as an acetic acid solution. Colposcopic grading is based solidly on visual examination, and the detected lesions are classified according to empirically qualitative scales. Clinical diagnosis based on the visual assessment (colposcopy) features a sensitivity of 0.77 and a specificity of 0.64 [Mitchell M F, et al. (1998) *Obstetrics & Gynecology*, 91:626-631]. Conventional colposcopy fails to diagnose 56% of microinvasive and 30% of invasive cervical cancer, leading to an inability to treat the lesion at its curable state. In addition, there is a high level of disagreement among physicians in identifying sites with high grade neoplasias for biopsy. Researchers have reported a considerable inter-observer variability in identifying cervical lesions through colposcopy [Schiffman M, et al. (2003) *Arch. Pathol. Lab. Med.*, 127: 946-949; NHS Report. Cervical Screening Programme, England: 2003-04 Statistical Bulletin 2004/20. October 2004. U.K.; and Cantor S B, et al. (1998) *Obstetrics & Gynecology*, 91;(2): 270-277]. This diminishes the reproducibility of colposcopy and it is mainly attributed to the fact that the colposcopic assessment is qualitative and subjective.

In order to obtain more accurate Cervical Intraepithelial Neoplasia (CIN) diagnosis and grading, biopsy samples are obtained from suspicious areas, which are then submitted for histological examination. Biopsy sampling poses several problems though, such as: a) subjectivity and high inter-observer disagreement (>30%), as revealed by the studies of Ismail et al. [Ismail S M, et al. (1989) *British Medical Journal*, 298;(6675): 707-710] Bellina et al. [Bellina J H, et al. (1982) *South Med. J.*, 75;(1): 6-8. 56] and Robertson et al. [Robertson A J, et al. (1989) *J. Clin. Pathol.*, 42;(3): 231-238], and b) risks of sampling errors in selecting an abnormal site for biopsy.

The existing diagnostic chain for cervical neoplasia has reduced the incidence and mortality to historically low levels but further substantial reduction seems unlikely with the existing diagnostic procedures. This fact highlights the need for alternative, more efficient technologies, implementing the stand alone, and single step "see and treat" concept.

Over the last decade there has been a considerable effort towards the development of novel optical technologies capable of providing improved and objective information for tissue pathology. These approaches are usually based on the fact that a tissue change from a normal to pathologic condition alters the tissue's structure and functionality, and these alterations can be detected in vivo, by exploiting the light-tissue interaction phenomena. The measurement and analysis of the characteristics of the remitted light from the tissue can also provide information about the presence of different molecules, or about the various structural and functional changes occurring during the progress of the disease, thus providing a means for the in vivo identification and grading of the lesion.

Previous attempts towards this direction include a variety of spectroscopic and spectral imaging techniques targeting the detection of biochemical and/or structural alterations in vivo. Indicatively, U.S. Pat. No. 4,930,516 discloses a method for detecting cancerous tissue, where a tissue sample is illuminated with excitation light at a first wavelength, producing a fluorescent radiation in response to the excitation light detected. The discrimination between cancerous tissue vs. normal tissue is based on the wavelength and amplitude of the emitted fluorescent radiation. Alternatively, the spectral amplitude of normal tissue will differ from that of a cancerous tissue at the same wavelength.

It is known that time resolved spectroscopy, which is based on monitoring the fluorescent decay time, has also a potential in discriminating the type, or condition, of an illuminated tissue. For example, U.S. Pat. No. 5,562,100 discloses a method for determining tissue characteristics based on illuminating a target tissue with a short pulse of excitation radiation at a particular wavelength, and detecting fluorescent radiation emitted by the target tissue in response to the excitation. Tissue characteristics are determined from the recorded amplitude of the emitted radiation. In a similar manner, U.S. Pat. No. 5,467,767 discloses a method for determining the malignant condition of a tissue, using time-resolved fluorescence spectroscopy.

Other methodologies focus on combining two or more measurement techniques to determine tissue characteristics. For instance, U.S. Pat. No. 6,975,899 discloses an apparatus and method utilizing fluorescence in combination with reflectance in order to de-couple the biochemical changes from the morphological changes occurring in a cancerous tissue. This combined approach is based on the fact that as tissue undergoes changes from a normal to a cancerous condition, fluorescence spectroscopy becomes less effective in determining tissue characteristics, as compared to absorption spectroscopy.

Other patents, such as U.S. Pat. No. 5,369,496, disclose a method and apparatus for diagnostic multispectral digital imaging using fluorescence, reflectance, and polarized reflectance spectroscopy. In U.S. Pat. No. 6,427,082 a method and a system is provided for discriminating healthy from pathologic cervical tissue based on the fluorescence response of the tissue to laser excitation (LIF), and the back-scattered response to illumination by white light.

In general, prior art spectroscopic methods focus on tissue characteristics at a limited number of points on the tissue, whereas optical imaging methods focus on time-independent measurements of optical parameters over the entire tissue area. Moreover, these methods provide information only for the altered biochemical or cellular tissue structure, and not for the altered functionality of the epithelium.

Another approach developed by C. Balas is substantially different than the conventional methodologies because it involves measuring quantitatively the dynamic phenomena occurring in tissues after the application of biomarkers (PCT Publication No. WO 01/72214 A1 [Balas C. (2001) *IEEE Trans. on Biomedical Engineering*, 48:96-104], and [Balas C J, et al. (1999) *SPIE* 3568: 31-37]). Measurements of the dynamic phenomena could potentially provide information for both structural and functional features of the tissue, facilitating an in vivo diagnosis.

Optical biomarkers are chemical substances that induce impermanent alterations of the optical response of the abnormal tissue. In the case of efficient biomarkers, the structural, morphological and functional alterations of the abnormal tissue are manifested in the optical signal generated during the biomarker tissue interaction facilitating lesion identification and localization.

A typical diagnostic procedure involving biomarker application includes administrating topically or systematically one or more biomarkers to tissue. Then, biomarker induced alterations in the optical properties of the tissue are visually observed qualitatively. Based on these alterations in the optical properties due to administration of the biomarker, abnormal areas are identified for diagnosis and treatment. Traditional diagnostic methods involving biomarkers suffer from several drawbacks mainly related to the fact that the visual assessment of dynamic optical phenomena cannot be effective, due to physiological limitations of the human optical system in quantitatively detecting and recording fast changing phenomena with different kinetics in different tissue sites.

The method and device disclosed in the aforementioned Balas reference relies on the administration of a pathology differentiating agent (biomarker), which has the property of enhancing the visualization of the altered structure and functionality of the abnormal cells selectively, and then the measurement at any spatial point and in various wavelength bands, the remitted light as a function of time. The recorded intensity of the remitted light (for example intensity of backscattered light (IBSL), defuse reflectance (DR) and fluorescence intensity), as a function of time is defined as the 'Dynamic Optical Curve' (DOC), which expresses the temporal characteristics of the optical phenomena generated during the tissue-biomarker interaction. Modeling and analysis of the acquired DOC enables calculation of a variety of Dynamic Optical Parameters (DOPs) which characterize the biomarker-tissue interaction kinetics at every image location (pixel or group of pixels) which corresponds to a tissue location. The spatial distribution of these parameters comprises the kinetic map, which can be overlaid onto the color image of the tissue. These data could potentially provide a means for the in vivo detection, mapping and grading of the lesion for diagnosis, screening, and follow up, while simultaneously enabling guidance for biopsy sampling, and surgical treatment.

Typically, the clinical value of a diagnostic technique is partially determined by its performance both in terms of its sensitivity (SS) and specificity (SP) positive and negative predictive value. If the SS and SP are greater than those of the existing diagnostic methods, then a new method or procedure could be deemed suitable for screening and/or clinical diagnosis purposes.

SUMMARY

Embodiments described herein include methods for determining tissue characteristics, like structural characteristics, functional characteristics and/or a pathological status of the tissue. Exemplary methods include generating data for a period of time based on an optical property of a tissue, or a portion thereof, that has been exposed to a biomarker. A value of a dynamic optical parameter is determined from the generated data. A tissue characteristic is determined by comparing the value of the dynamic optical parameter with at least one reference value of the dynamic optical parameter, where the at least one reference value is known to be linked to a tissue characteristic. Specifically, embodiments of the present invention provide methods for automated diagnosis of tissue for screening purposes, or for semi-automated diagnosis of tissue, based on selecting one or more appropriate dynamic optical parameters (DOPs), along with the corresponding cut-off values for each parameter that best discriminate various pathologic conditions. This is achieved via correlation of the DOPs, extracted from the dynamic optical curve (DOC), with both qualitative and quantitative pathology. Embodiments of the invention disclosed herein also provide methods for assessing both structural and functional features in a living tissue via modelling of epithelial transport phenomena, and the correlation of epithelial transport phenomena with in vivo measured dynamic optical characteristics.

Embodiments include a method, which may be automated or semi-automated method, for characterizing (e.g., grading) a tissue, such as, for example, a cancerous or pre-cancerous tissue (e.g., of a cervical, uterine, oral, skin, respiratory, and gastrointestinal cancerous and/or pre-cancerous tissue). Thus, in a first aspect the invention provides a method for determining tissue characteristics. Tissue characteristics include structural tissue characteristics, functional tissue characteristics, and a pathological status of the tissue. The method includes generating data for a dynamic optical curve over a period of time based on an optical property of a tissue, or portion thereof, that has been exposed to a biomarker. The method further includes determining a value of a dynamic optical parameter based on said data. The method also includes comparing the value of the dynamic optical parameter with at least one reference value of the dynamic optical parameter known to be linked to a tissue characteristic. The method still further includes determining a tissue characteristic, or portion thereof, based on the comparison.

Methods of the present invention are useful in, for example, facilitating the screening, clinical diagnosis, guided biopsy sampling or treatment of a tissue. The tissue may be an epithelial pre-cancer tissue or a cervical, uterine, oral, skin, respiratory or gastrointestinal pre-cancerous or cancerous tissue. Exemplary methods include plotting a dynamic optical curve based on the intensity of backscattered light from a tissue, or portion thereof, that has been exposed to a biomarker over time. The exemplary methods further include based on the dynamic optical curve, determining a dynamic optical parameter, e.g., 'Integral', 'Max', 'Time to Max', 'Area to Max', 'SlopeA', and 'SlopeB', and characterizing the tissue based on the value of one or more of the dynamic optical parameters or sub-combinations thereof. The dynamic optical curve may represent the temporal variation of the intensity of the back-scattered light obtained from a tissue site after application of a biomarker and the dynamic optical parameter may be derived via a mathematical analysis of one or more of the dynamic optical curves or via empirical, manual, or visual analysis of one or more of the dynamic optical curves.

In one embodiment, the tissue under test is a cervical tissue. In a further embodiment, exemplary methods are used to diagnose or characterize a neoplasia and/or to detect an HPV infection. In another embodiment, exemplary methods are used to determine the nuclear to cytoplasmic ratio of the cells of the tissue for tissue that includes epithelial cells.

The methods of embodiments of the present invention achieve at least 60% sensitivity and at least 60% specificity, even more preferably at least 65% sensitivity and at least 65% specificity, and most preferably at least 75% sensitivity and at least 75% specificity.

In one embodiment, the biomarker is selected from a solution of acetic acid (e.g., a 3-5% acetic acid solution), formic acid, propionic acid, butyric acid, Lugol's iodine, Shiller's iodine, methylene blue, toluidine blue, osmotic agents, ionic agents, and indigo carmine.

In another embodiment, the dynamic optical parameter is the 'Integral' and a value greater than or about equal to an 'Integral' cut-off value indicates that the cervical tissue being tested is a high grade cervical neoplasia (e.g., distinguishes a high grade cervical neoplasia from a low grade cervical neoplasia), where the 'Integral' cut off value is between about 480 and about 650 normalized (dimensionless), (e.g., about 480, 490, 500, 510, 520, 530, 540, 550, 560, 570, 580, 590, 600, 610, 620, 630, 640 or 650). Although increments of 10 units are recited for a cut-off value, one of ordinary skill in the art will recognize that the chosen increments for any of the cut-off values for the various dimensionless dynamic optical parameters may be larger or smaller than 10 units.

In a further embodiment, the dynamic optical parameter is the 'Integral' and a less than or about equal to a different 'Integral' cut-off value indicates that an HPV infection is the cause of said cervical cancer tissue (e.g., distinguishes an HPV infection from a high grade cervical neoplasia), where the different 'Integral' cut-off value is between about 420 and about 490 normalized (dimensionless) (e.g., about 420, 430, 440, 450, 460, 470, 480, 485 or 490).

In yet another embodiment, the dynamic optical parameter is the 'Max' and a value greater than or about equal to a 'Max' cut-off value indicates that said cervical cancer tissue is a high grade cervical neoplasia (e.g., distinguishes a high grade cervical neoplasia from a low grade cervical neoplasia), where the "Max' cut-off value is between about 70 and about 90 calibrated units (e.g., about 70, 75, 80, 85, 86, 87, 88, 89 or 90).

In a further embodiment, the dynamic optical parameter is the 'Max' and a value less than or about equal to a different 'Max' cut-off value for an HPV infection, indicates that an HPV infection is the cause of said cervical cancer tissue (e.g., distinguishes an HPV infection from a high grade cervical neoplasia), where the different 'Max' cut-off value is between about 65 and about 90 calibrated units (e.g., about 60, 65, 70, 75, 80, 85, 86, 87, 88, 89 or 90).

In yet another embodiment, the dynamic optical parameter is the Time to Max and a value greater than or about equal to a 'Tmax' cut-off value indicates that the cervical tissue being tested is a high grade cervical neoplasia (e.g., distinguishes a high grade cervical neoplasia from a non high grade cervical neoplasia ), where the 'Tmax' cut-off values is between about 80 and about 100 sec.

In yet another embodiment, the dynamic optical parameter is the 'Area to Max' and a value greater than or about equal to an 'Area to Max' cut-off value for a high grade cervical neoplasia, indicates that said cervical cancer tissue is a high grade cervical neoplasia (e.g., distinguishes a high grade cervical neoplasia from a low grade cervical neoplasia), where the 'Area to Max' cut-off value is between about 120 and about 170 normalized, (dimensionless) (e.g., about 120, 130, 140, 150, 160 or 170).

In yet another embodiment, the dynamic optical parameter is the SlopeA and a value greater than or about equal to a 'SlopeA' cut-off value, indicates that said cervical cancer tissue is a high grade cervical neoplasia (e.g., distinguishes a high grade cervical neoplasia from a low grade cervical neoplasia), where the 'SlopeA' cutoff value is between about 1.1 and about 1.3 (red) (e.g., about 1.1, 1.2 or 1.3 red).

In yet another embodiment, the dynamic optical parameter is the 'SlopeB' and a value less than or about equal to a 'SlopeB' cut-off value indicates that said cervical cancer tissue is a high grade cervical neoplasia (e.g., distinguishes a high grade cervical neoplasia from a low grade cervical neoplasia), where the 'SlopeB' cutoff value is between about −0.012 and about −0.090 (red) (e.g., −0.012, −0.020, −0.025, −0.030, −0.040, −0.050, −0.060, −0.070, −0.080, or −0.090).

An exemplary embodiment of the invention is a method for characterizing a cervical tissue, such as a cervical cancer, or a pre-cancer tissue by plotting a dynamic optical curve based on an optical property observed from an imaged cervical tissue (for example the intensity of backscattered light (IOBL) from a cervical cancer or pre-cancer tissue) or portion thereof, that has been exposed to a biomarker over time. Then, based on the dynamic optical curve, determining a dynamic optical parameter selected from the group consisting of 'Integral', 'Max', 'Time to Max', 'Area to Max', 'SlopeA', and 'SlopeB'; based on the value of one or more of the dynamic optical parameters or sub-combinations thereof characterizing the cervical cancer or pre-cancer tissue.

An exemplary embodiment is a method for characterizing a tissue that includes administering a biomarker to a tissue, e.g., by means of an applicator, according to aspects of the present invention. The method further includes capturing a series of spectral and color images over a predetermined time period, before and after the biomarker administration with proper synchronization between biomarker administration and initiation of image capturing, and aligning said images. The method also includes calculating from the series of spectral and color images a dynamic optical curve at every image point and expressing the remitted light as a function of time for a predetermined spectral band. The method further includes calculating one or more dynamic optical parameters from the dynamic optical curves, and displaying the one or more dynamic optical parameters in the form of a pseudocolor map, thereby characterizing a tissue.

Another exemplary embodiment is a method for determining in vivo functional and structural characteristics of a tissue, according to other aspects of the present invention. The method includes administering a biomarker to a tissue, e.g., by means of an applicator and capturing a series of spectral and color images in time succession and over a predetermined time period, before and after the biomarker administration and with proper synchronization between biomarker administration and initiation of image capturing. Said images may be aligned. The method also includes calculating a dynamic optical curve for a predetermined spectral band at selected image points or at every image point from the series of spectral and color images, where the dynamic optical curve expresses one or more optical characteristics of the tissue, such as the remitted light as a function of time. The method further includes calculating one or more dynamic optical parameters (e.g., 'Integral', 'Max', 'Time to Max', 'Area to Max', 'SlopeA', and 'SlopeB') from the data (i.e. the dynamic optical curves). The method further includes displaying the one or more dynamic optical parameters in the form of a pseudocolor map, thereby determining in vivo functional and structural characteristics of a tissue.

It is confirmed that all embodiments taught or suggested in respect of the various aspects of the present invention apply mutatis mutandis to the other related aspects of the present invention and are not repeated for reasons of conciseness.

In one embodiment, the dynamic optical parameter 'Integral' is used to obtain information for the functional and structural characteristics of the tissue. In another embodiment, the dynamic optical parameter is 'Max' and the functional and structural characteristics of the tissue are selected from the group consisting of extra cellular acidity, passive diffusion constant, number of cell layers of the stratified epithelium, and nuclear-to-cytoplasm-ratio.

In a further embodiment, the mathematical formulas correlating the nuclear-to-cytoplasm-ratio (NCR) with the 'Integral' and 'Max' parameters are:

$$NCR = 1/1349 \times Integral - 0.278 \text{ and } NCR = 1/181 \times Max - 0.309.$$

In yet another embodiment, the dynamic optical parameter is 'SlopeA' and the functional and structural characteristics of the tissue are selected from the group consisting of cell malfunction in regulating the intracellular pH, existence of disorganized vasculature, and poor lymphatic drainage.

In related aspects, embodiments also provides a computer readable medium holding computer program instructions for characterizing a tissue, which when executed by a computing device causes the computing device to perform the steps for characterizing a tissue. The steps include calculating from a series of spectral and color images a dynamic optical curve at selected image points expressing remitted light as a function of time at a predetermined spectral band, after application of a biomarker. The steps also include determining one or more dynamic optical parameters from the dynamic optical curves. The steps further include storing said one or more dynamic optical parameters for use in characterizing a cancer tissue.

In a preferred embodiment, the dynamic optical parameters are used for discriminating pathologic conditions via combination of dynamic optical parameters with the aid of an Artificial Neural Network, statistical pattern recognition algorithm, Bayesian classification, or classification trees.

In a further aspect, there is provided a computer readable medium holding computer executable instructions for performing a method for characterizing a tissue. The method includes determining data for a dynamic optical curve from a captured optical property of a tissue, or portion thereof, that has been exposed to a biomarker over time. The method also includes determining a dynamic optical parameter based on said data. The method further includes characterizing said tissue based on the value of one or more of said dynamic optical parameters or sub-combinations thereof.

Similarly, embodiments of the present invention include a computer readable medium holding computer executable instructions for characterizing a cervical tissue. The instructions including instructions for plotting a dynamic optical curve based on one or more optical properties of a cervical tissue, or portion thereof, that has been exposed to a biomarker over time. The instructions also including instructions for determining a dynamic optical parameter selected from the group consisting of 'Integral', 'Max', 'Time to Max', 'Area to Max', 'SlopeA', and 'SlopeB' based on said dynamic optical curve, and characterizing said cervical tissue based on the value of one or more of said dynamic optical parameters or sub-combinations thereof.

There is also provided a computer readable medium holding computer executable instructions for performing a method for characterizing a tissue. The method including the steps of administering a biomarker to a tissue, and capturing a series of spectral and color images in time succession and for a predetermined time period, before and after the biomarker administration and with proper synchronization between biomarker administration and initiation of image capturing. The method further including the steps of calculating from the series of spectral and color images a dynamic optical curve at selected image points, and expressing an optical property as a function of time at a predetermined spectral band. The method further including the steps of calculating one or more dynamic optical parameters from the dynamic optical curves and displaying said one or more dynamic optical parameters in the form of a pseudocolor map, thereby characterizing a cancer tissue.

Further provided herein is a computer readable medium holding computer executable instructions for performing a method for determining in vivo functional and structural characteristics of a tissue. The method including the steps of administering a biomarker to a tissue, and capturing and aligning a series of spectral and color images in time succession and for a predetermined time period, before and after the biomarker administration and with proper synchronization between biomarker administration and initiation of image capturing. The method also including the steps of calculating from the series of spectral and color images a dynamic optical curve at every image point, expressing remitted light as a function of time, at predetermined spectral band. The method further includes the steps of calculating one or more dynamic optical parameters from the dynamic optical curves, and displaying said one or more dynamic optical parameters in the form of a pseudocolor map, thereby determining in vivo functional and structural characteristics of a tissue.

All appropriate embodiments relating to the methods of the invention apply mutatis mutandis to the computer readable medium aspects of the invention. Other features and advantages of exemplary embodiments of the invention will be apparent from the following detailed description and claims.

BRIEF DESCRIPTION OF THE FIGURES

Embodiments of the invention will now be described with reference to the following drawings, and the claims. In the drawings, like reference numerals are used to refer to like elements throughout the various views.

DETAILED DESCRIPTION

Figure 1:
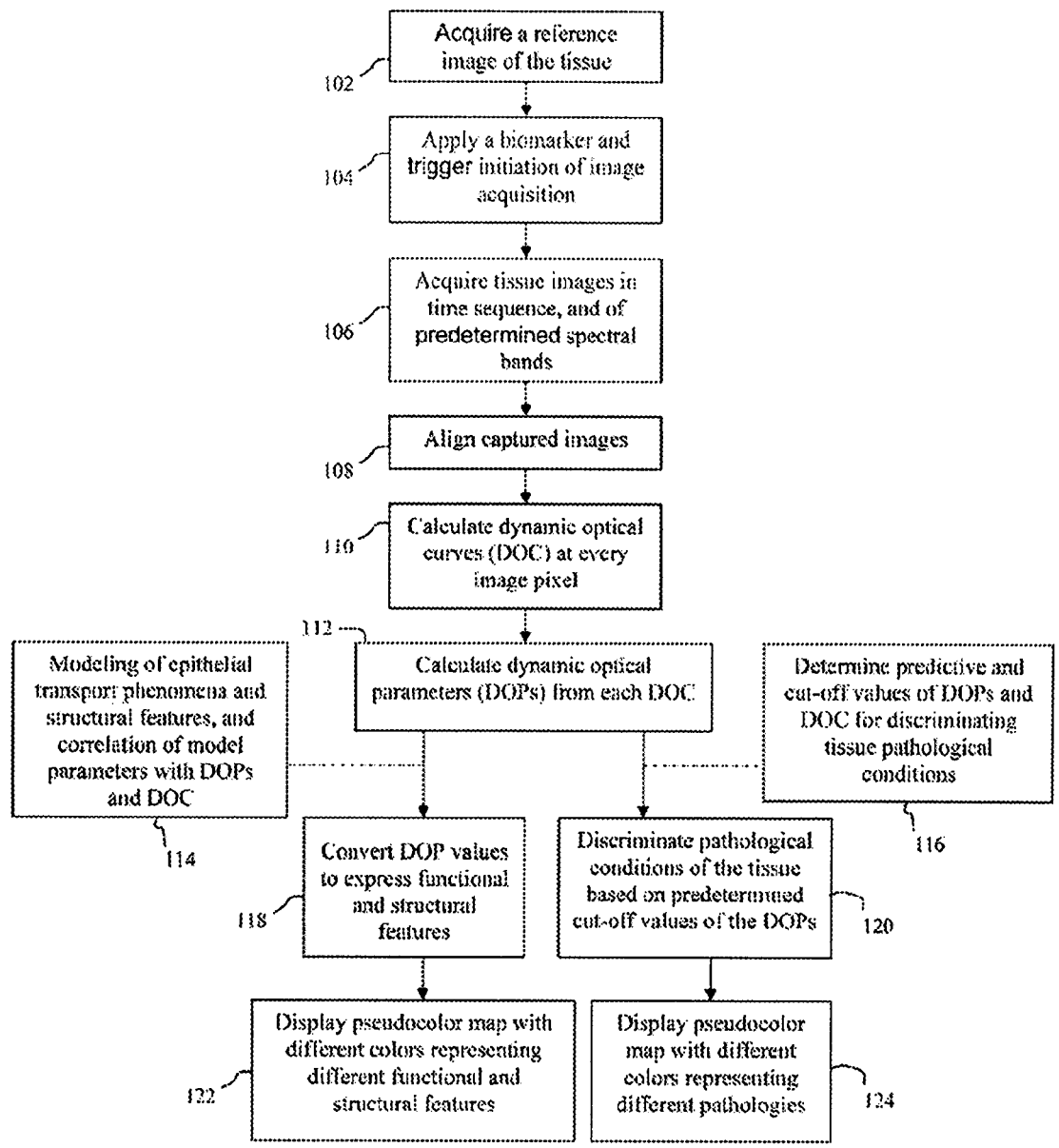
FIG. 1 is an illustration of the flowchart of the diagnostic method disclosed herein.

Embodiments of the present invention provide a method for systematic parametric analysis of a dynamic optical curve (DOC) to produce dynamic optical parameters (DOPs). Embodiments also provide a method for generating reference values for DOPs which relate measured DOP values to tissue characteristics (e.g. structural characteristics, functional characteristics and/or a pathological status of a tissue). Embodiments also provide a method for comparative evaluation of the derived DOPs in terms of both predictive value and efficiency in discriminating various normal and pathologic conditions.

Embodiments of the present invention provide for a quantitative determination of tissue characteristics that is particularly suited to automated or semi-automated processes. One embodiment includes method for automated diagnosis for screening purposes or for semi-automated clinical diagnosis in colposcopy, based on selecting appropriate DOPs, along with their corresponding cut-off values, that best discriminate various pathologic conditions. This is achieved via correlation of the DOPs, extracted from the DOC, with both qualitative and quantitative pathology.

Exemplary methods allow determination of spatial features and the spatial extent of abnormal tissue. These methods include imaging an area of tissue over time and calculating a DOC for each tissue location (pixel or specified group of pixels). Then, values for one or more relevant DOP are calculated from the DOC at each tissue location. The calculated values for the one or more relevant DOP are compared to reference values for the one or more relevant DOPs. Based on the comparison, tissue characteristics, such as pathological status, are determined for each tissue location, from which a map of pathological status for each tissue location may be generated.

Exemplary methods of the present invention correlate in vivo measured dynamic optical characteristics with epithelial transport phenomena. Modelling of the epithelial transport phenomena provides information regarding structural and functional features in a living tissue. The correlation and the modelling allow measurements of in vivo measured dynamic optical characteristics to be related to structural and functional features of living tissue.

As used interchangeably herein, the terms "dynamic optical curve" or "DOC" are intended to include a curve representing an optical characteristic of tissue under observation, including, but not limited to intensity of backscattered light from a tissue or portion thereof, reflectance of light, diffusive reflectance of light from a tissue or a portion thereof, or fluorescence from a tissue or a portion thereof that has been exposed to a biomarker over time.

As used herein, the term "biomarker" is intended to include any chemical agent capable of altering an optical signal from the tissue sample being tested. Non-limiting examples of such agents include, but are not limited to acetic acid, formic acid, propionic acid, butyric acid, Lugol's iodine, Shiller's iodine, methylene blue, toluidine blue, osmotic agents, ionic agents, and indigo carmine. Any solutions of the foregoing agents may be used. In a preferred embodiment, the biomarker is an acetic acid solution, e.g., a 3-5% acetic acid solution.

As used herein, the term "dynamic optical parameter" is intended to include the one or more parameters, derived from optical measurements, based on which a tissue may be characterized. As described herein such parameters may be derived via a mathematical analysis of one or more of the dynamic optical curves plotted based on the intensity of backscattered light from a cancer tissue, or portion thereof, that has been exposed to a biomarker over time. Such parameters may also be derived by an empirical, manual, or visual analysis of one or more of said dynamic optical curves. Non-limiting examples of the dynamic optical parameters contemplated by the present invention are 'Integral', 'Max', 'Time to Max' ('Tmax'), 'Area to Max', 'SlopeA', and 'SlopeB'.

The articles "a" and "an" are used herein to refer to one or to more than one (i.e. to at least one) of the grammatical object of the article. By way of example, "a dynamic optical parameter" means one or more dynamic optical parameters.

As used herein, the term "tissue" is intended to include any tissue, or portions thereof, including cancerous and pre-cancerous tissues. For example, the tissue may be an epithelial tissue, a connective tissue, a muscular tissue or a nervous tissue. In a preferred embodiment of the invention, the tissue is an epithelial tissue, or a portion thereof, e.g., covering and lining epithelium or glandular epithelium. For example, the tissue may be cervical tissue; skin tissue; gastrointestinal tract tissue, e.g., oral cavity tissue, stomach tissue, esophageal tissue, duodenal tissue, small intestine tissue, large intestine tissue, pancreatic tissue, liver tissue, gallbladder tissue or colon tissue; or nasal cavity tissue. In one embodiment, the tissue is a pre-cancer or cancer tissue, such as, for example, a dysplasia, a neoplasia or a cancerous lesion.

As used herein, the phrase "characterizing" a cancer tissue is intended to include the characterization of a cancer tissue using the methods described herein such that the screening, clinical diagnosis, guided biopsy sampling and/or treatment of a cancer tissue is facilitated. For example, a cancer tissue may be graded, e.g., characterized as a low grade (LG) lesion (i.e., an HPV infection, an inflammation or a CIN Grade I lesion, or a sub combination thereof) or a high grade (HG) lesion (i.e., a CIN Grade II lesion, a CIN Grade III lesion, or Invasive Carcinoma (CA) or a subcombination thereof).

As used herein, tissue characteristics include, but are not limited to, structural characteristics, functional characteristics and a pathological status of a tissue, as well as any combination of the aforementioned.

As used herein, "Reference values" relate to predictive and cut-off values of the various dynamic optical parameters (DOPs) which correlate with and can be used to discriminate specific tissue pathological conditions and/or structural and functional characteristics of a tissue.

There are different systems for characterizing and classifying various degrees of cervical intraepithelial neoplasia (CIN), formerly called dysplasia. Histologically evaluated lesions are typically characterized using the CIN nomenclature; cytologic smears are typically classified according to the Bethesda system; and cervical cancer is typically staged based on the International Federation of Gynecology and Obstetrics (FIGO) system. CIN Grade I (mild dysplasia) is defined as the disordered growth of the lower third of the epithelial lining; CIN Grade II (moderate dysplasia) is defined as the abnormal maturation of two-thirds of the lining; CIN Grade III (severe dysplasia): encompasses more than two thirds of the epithelial thickness with carcinoma in situ (CIS) representing full-thickness dysmaturity. There are well known classification systems for the characterization of cervical dysplasia, i.e., the disordered growth and development of the epithelial lining of the cervix (see, for example, DeCherney, A. et al., *Current Obstetric & Gynecologic Diagnosis & Treatment*, 9th ed., The McGraw-Hill Companies, New York, N.Y. (2003), the contents of which are incorporated herein by reference).

FIG. 1 illustrates an exemplary quantitative method for determining tissue characteristics. A reference image of the tissue is acquired (step 102). The reference image records the original optical properties of the examined tissue. A biomarker is applied (step 104). The biomarker may be applied by an applicator that provides a triggering signal to initiate image acquisition, right after biomarker application (i.e., less than 1 second), thus ensuring the synchronization and the standardization of the acquisition process. Alternately, initiating image acquisition may trigger biomarker application, or an externally generated signal may trigger both initiation of image acquisition and biomarker application. After biomarker application, a series of images are acquired at a predetermined acquisition rate, at one or more predetermined spectral bands for a predetermined time period (step 106). The image acquisition rate may be between one image every five seconds and one image every seven seconds. The total time period for acquisition after application of the biomarker may be about four minutes. The time period for image acquisition is determined taking into account the duration of the optical phenomena induced by the biomarker. Those skilled in the art will recognize that the time period can extend beyond four minutes to one or two hours or any time interval therebetween, but factors such as patient comfort, patient convenience, effectiveness of optical phenomena induced by the biomarker beyond a certain period, system capabilities such as storage capacity and processing capacity, and other like factors can be used to determine a desired time period. For optical phenomena with a short duration the predetermined time period for image may be shorter than four minutes. Alternatively, the time period can be measured in terms of the number of images acquired, for example, thirty images, thirty-five images, forty images and the like. Spectral bands are selected such that maximum contrast between biomarker responsive and non responsive areas is achieved.

The series of captured images may be aligned (step 108). Alignment ensures that image pixels corresponding to a specific image location in each image correspond to the same tissue point. The images may already be aligned after acquisition because the detector did not move relative to the tissue during image acquisition, however, if the images are not already aligned, an alignment step must be performed to obtain the temporal variation of light intensity emitted by every tissue point. For accurate temporal variation measurements image pixels corresponding to a specific image location need to correspond to the same tissue point in each image taken at different points in time.

In many types of in vivo measurements, the optical sensor (detector) will measurably move relative to the tissue due to breathing, etc, during successive acquisition of tissue images. Constant relative position between the optical sensor and the examined tissue area may be ensured, for example, through either mechanical stabilization means, and/or image registration algorithms. The captured images must also be aligned with the reference image to ensure valid extraction of the dynamic optical curve from every image pixel or group of pixels corresponding to a specific location of the examined tissue.

The dynamic optical curve (DOC) is calculated from some or all of said acquired series of images at every image location (i.e., every pixel location or a location defined by a group of pixels) within a region of interest (step 110). All of the pixels in the detector may be included in the region of interest, alternately, the region of interest may include only a selected portion (area) of the image of the tissue. Each DOC expresses an optical property such as the diffuse reflectance [DR], or fluorescence intensity (FI), as a function of time at a predetermined spectral band. More than one spectral band may be imaged simultaneously. The selection of the optical property to be measured is determined by the properties of the employed biomarker that alters one or more optical properties of the tissue, either the diffuse reflectance, or fluorescence characteristics, respectively. As indicated above, proper spectral bands are selected depending on the tissue being imaged, the biomarker employed and the characteristic of the light source employed, to provide maximum contrast between biomarker responsive and non-responsive tissues and tissue areas.

One or more dynamic optical parameter (DOPs) are calculated from the dynamic optical curve (DOC) obtained from each image location (i.e., every pixel location or a location defined by a group of pixels) for selected images, (step 112). The DOPs derived from a DOC express the dynamic characteristics of the interaction between the biomarker and the tissue.

An embodiment of the present invention relates one or more DOPs for a tissue location to a tissue pathology at that tissue location for generating a spatial map of tissue pathologies. Depending on the efficiency of the biomarker in selectively staining tissue abnormalities, DOPs can provide a quantitative means for assessing in vivo various tissue pathologies. The values of a particular DOP for each tissue locations can be displayed in the form of a pseudocolor map, with different colors representing different parameter values. DOPs that can be quantitatively related to tissue pathologies can be used to generate a pseudocolor map of a lesion. Such pseudocolor maps can be used for determining a lesion's grade and margins, thus facilitating biopsy sampling, treatment, and lesion management in general.

To relate one or more DOSs to tissue pathologies, reference values for each of the one or more DOPs can be determined that relate a particular DOP to a particular tissue pathology, (step 116). A reference value may be an expected value of a DOP for a tissue with a particular tissue pathology. The reference value may be a cut-off value where a measured value of the DOP that falls on a particular side of the reference value indicates the existence of a particular tissue pathology. Alternatively, a measured values of the DOP that falls on a particular side of the reference value may indicate the absence of a particular tissue pathology. In one embodiment reference values of the one or more DOPs from a DOC are determined experimentally in a statistically sufficient tissue population by comparing measured values for one or more DOPs, calculated from DOCs recorded at one or more spectral bands, with standard methods providing definite diagnosis, such as histology (gold standards). Cut-off values that best discriminate various pathological conditions are determined for those DOPs displaying adequate reference values. For a specific biomarker and epithelial tissue the determination of reference values of the one or more DOPs can be performed separately and not as a part of the routine implementation of the method.

Once reference values of one or more DOPs that correlate a DOP with a pathological condition are calculated or otherwise provided, calculated values of one or more DOPs, based on a measured DOC, may be used to determine a pathological condition at a tissue location. A pathological condition at each location of the tissue is determined based on predetermined reference values of the one or more DOPs, (step 120). Analysis of the assessment of the reference values for various DOPs in the case where the tissue is cervical epithelium and the biomarker is acetic acid solution is provided below with reference to FIGS. 7 to 9.

DOP values at each tissue location representing different pathological conditions and grades can be displayed in a form of a pseudocolor map, wherein different colors represent different grades, (step 124). The pseudocolor map expresses a pathology map which can be used for the in vivo grading of the lesion, and the determination of the lesion margins, facilitating biopsy sampling, treatment and in general the management of the lesion.

In a different embodiment of the current invention, one or more DOPs calculated from each measured DOC are related to function characteristics of the imaged tissue and structural characteristics of the imaged tissue. Biophysical models of both transport phenomena and structural features of an epithelial tissue are developed based on the understanding and the analysis of biomarker-tissue interaction through in vivo and in vitro experiments, (step 114). In cases where epithelial transport phenomena are determined by the functional characteristics of the tissue and these characteristics are expressed in DOCs and associated DOPs, model parameters provide a means for the in vivo assessment of functional and structural characteristics of the tissue. In particular, DOP values may be converted to express functional and/or structural features of the tissue in various normal and pathological conditions, (step 118). It is worth noting that functional properties can be determined only in living tissues, whereas structural features can be determined in vitro by analyzing tissue samples (biopsies). The methods of the present invention provide a means for assessing both features in vivo, thus, enabling more complete epithelial system characterization or identification. Complete epithelial system characterization/identification is expected to improve diagnostic performance since various pathological conditions affect both functional and structural properties of an epithelial tissue. As an example, and referring to structural phenomena for the case of cervical cancer where acetic-acid solution is used as a biomarker, DOP values are correlated with quantitative data expressing nuclear density obtained through quantitative pathology methods. The correlation described below with reference to FIGS. 10A and 10B enables the conversion of DOP to nuclear-to-cytoplasmic-ratio. For either functional or structural features, a pseudocolor map may be generated with different colors representing different functional and structural features, (step 122). The pseudocolor map may express a tissue functionality and/or structural map, which can be used for the in vivo grading of the lesion, and the determination of the lesion margins, facilitating biopsy sampling, treatment and in general management of the lesion. The pseudocolor map may be also used for in vivo monitoring of the effects of the biomarker in both structural and functional features of the tissue and, consequently, for assessing the efficiency of the biomarker in highlighting abnormal tissue areas.

Some exemplary embodiments of present invention are described and demonstrated with respect to measurements of cervical tissue before and after application of an acetic acid solution biomarker. The choice of cervical tissue and acetic acid are solely for descriptive and illustrative purposes and are not meant to be limiting. One of ordinary skill in the art will recognize that other types of tissue and types of biomarkers fall within the scope of the present invention. The appropriate DOPs, and corresponding cut-off values were determined that best discriminate among tissue conditions/pathologies including normal, HPV (Human Papillomavirus) infection, Inflammation, and Cervical Intraepithelial Neoplasia (CIN) of different grades. Acetic acid solution 3-5% was used as the biomarker and the above mentioned measuring procedure for obtaining the DOC was followed. In order to determine the reference values of DOC and DOPs, experimental data were obtained from a multi-site clinical trial, where 308 women with abnormal Pap-test were enrolled and examined. DOCs were obtained though image capturing in time sequence of the cervical tissue in the blue-green spectral range. The acetic acid responsive tissue areas, as depicted by a DOC and DOPs pseudocolor map, were biopsied and submitted for histological evaluation and grading. The histology classification was then compared with a set of DOPs in order to determine the DOPs that best correlate with histology grading through Receiver Operator Characteristics (ROC) analysis. In signal detection theory, a receiver operating characteristic (ROC), or simply ROC curve, is a graphical plot of the sensitivity vs. (1-specificity) for a binary classifier system as its discrimination threshold is varied. The ROC can also be represented equivalently by plotting the fraction of true positives (TPR=true positive rate) vs. the fraction of false positives (FPR=false positive rate).

From the ROC curve, the optimum cut-off values for each parameter, or for a set of parameters, were derived providing the desirable SS and SP values.

Figure 5:
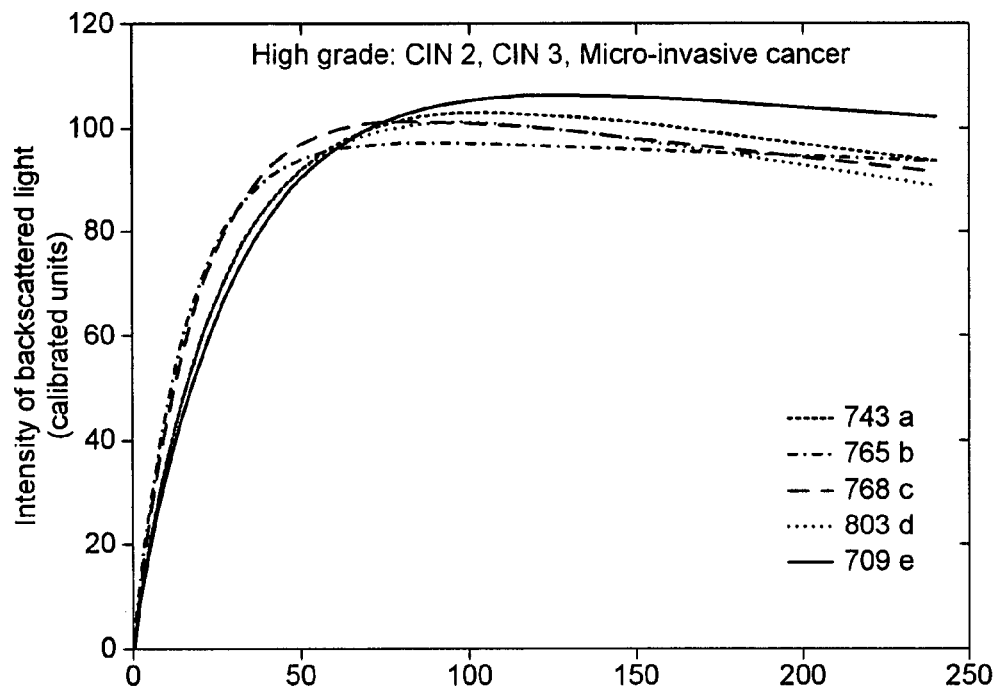
FIG. 5 shows exemplary DOCs obtained from cervical tissue sites interacting with acetic acid, corresponding to high-grade (HG) lesions (CIN II, III, micro invasive cancer), as classified by histology.
Figure 11:
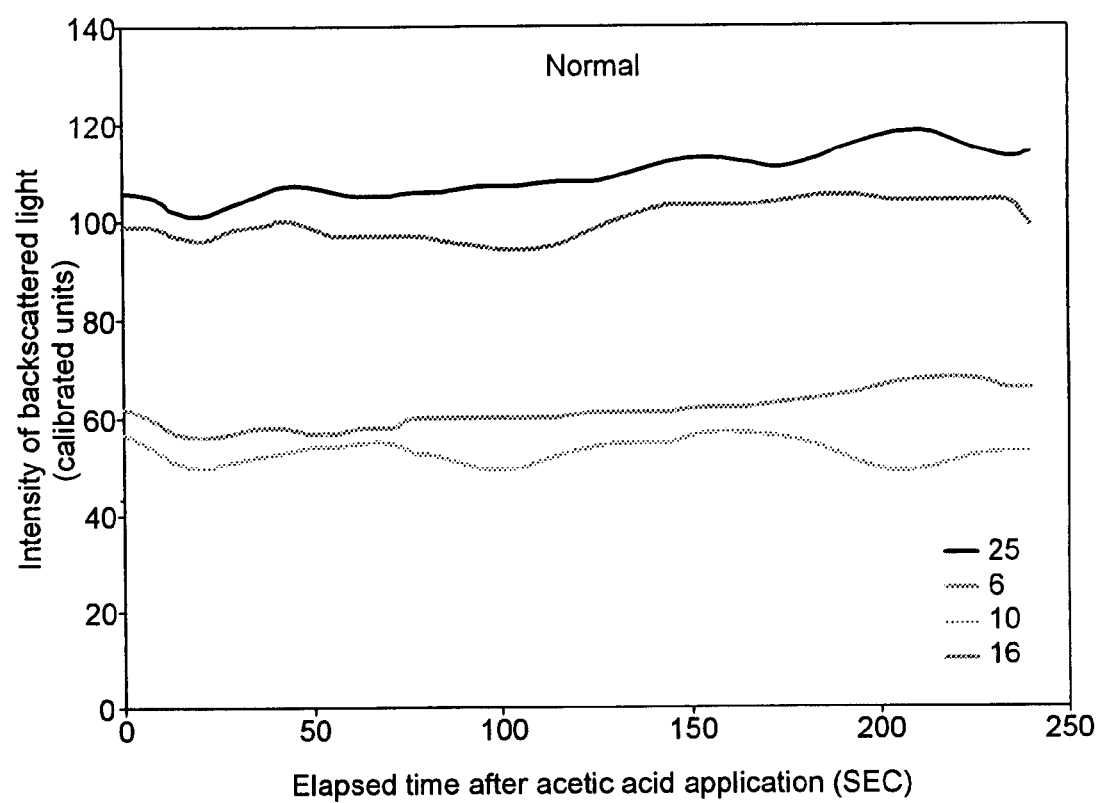
FIG. 11 shows exemplary DOCs obtained from cervical tissue sites interacting with acetic acid, corresponding to healthy (normal) tissue, as classified by histology.

In an illustrative embodiment, FIG. 2 to FIG. 5 show exemplary dynamic optical curves (DOCs) obtained from cervical tissue sites classified by the histologists as: HPV infection (FIG. 2), Inflammation (FIG. 3), CIN1 (FIG. 4), and high-grade (HG) lesions (FIG. 5). As a further categorisation used commonly in clinical practice, HPV, Inflammation, CIN1, or combination thereof, are referred to as low-grade (LG) lesions. HG lesions correspond to either, or combination of, CIN2, CIN3, or Invasive Carcinoma (CA). Histological grades CIN1, CIN2, and CIN3 are precursors of CA (CIN1- lowest, CIN3-highest). In each graph the vertical axis corresponds to the intensity of backscattered light (IBSL) (expressed in arbitrary units), and the horizontal axis represents elapsed time (in seconds) after the application of acetic acid to the tissue. The various traces a, b, c, d, e in each figure are DOCs from different cervical tissues. The number associated with each trace in each figure (e.g. a-510, b-740, c-500, d-519, and e-518 for FIG. 2) is the measurement of the 'Integral' for that trace (calculation of the 'Integral' is discussed below). The variation between DOCs corresponding to tissues with different pathologic conditions demonstrates that temporal alterations in backscatter intensity depend on the pathologic condition of the tissue. The DOCs for different types of abnormal tissue depicted in FIGS. 2 to 5 that show significant measureable changes in intensity with time are markedly different than DOCs obtained for normal tissue which are almost constant across the entire measurement period, (see FIG. 11). It is clearly seen that the DOCs corresponding to the various pathologic conditions, as well as normal tissue, differ in various ways in terms of intensity-temporal alterations.

Figure 2:
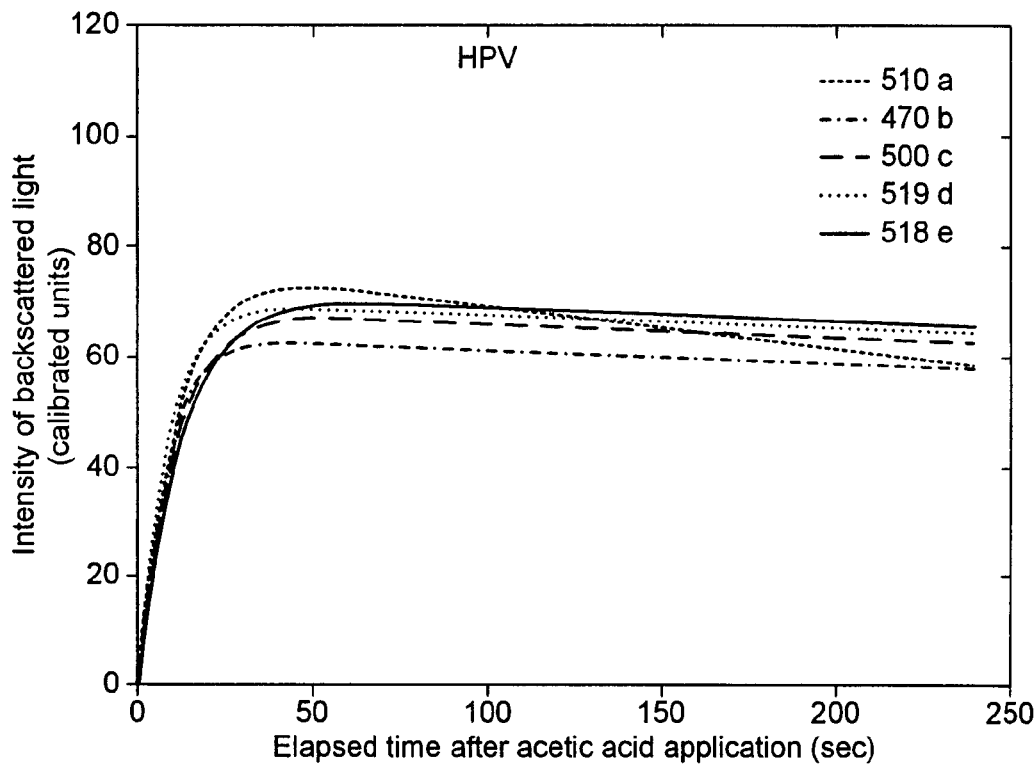
FIG. 2 shows exemplary dynamic optical curves (DOCs) obtained from cervical tissue sites interacting with acetic acid, corresponding to Human Papiloma Virus (HPV) infections, as classified by histology.
Figure 3:
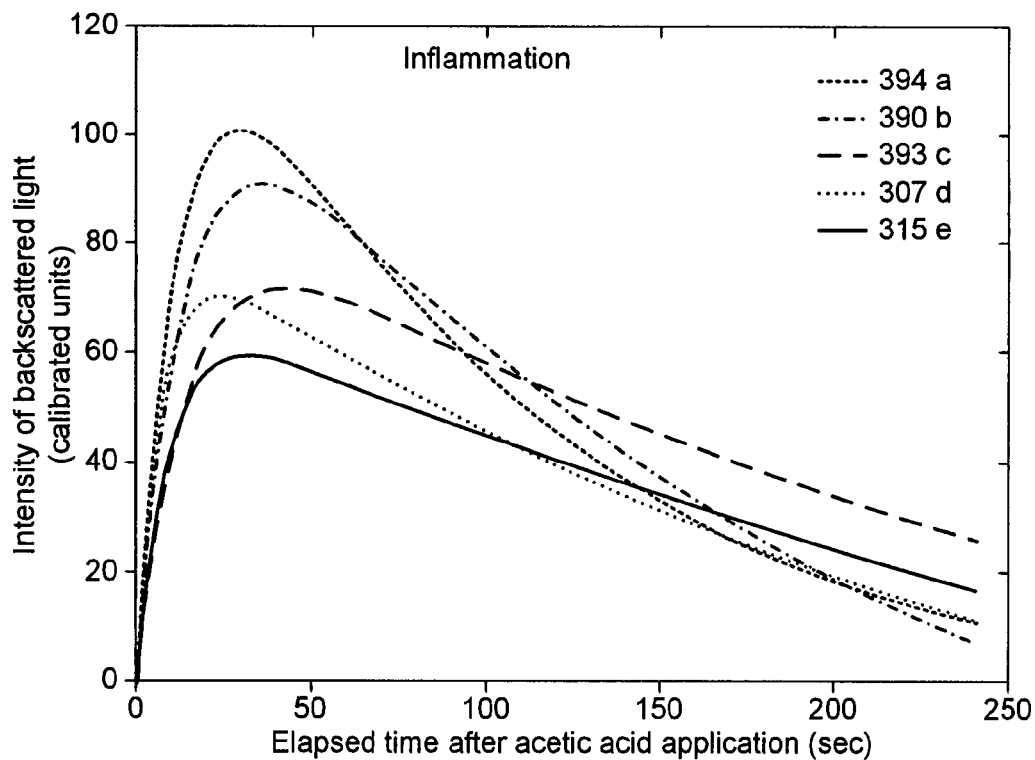
FIG. 3 shows exemplary DOCs obtained from cervical tissue sites interacting with acetic acid, corresponding to inflammation, as classified by histology.
Figure 4:
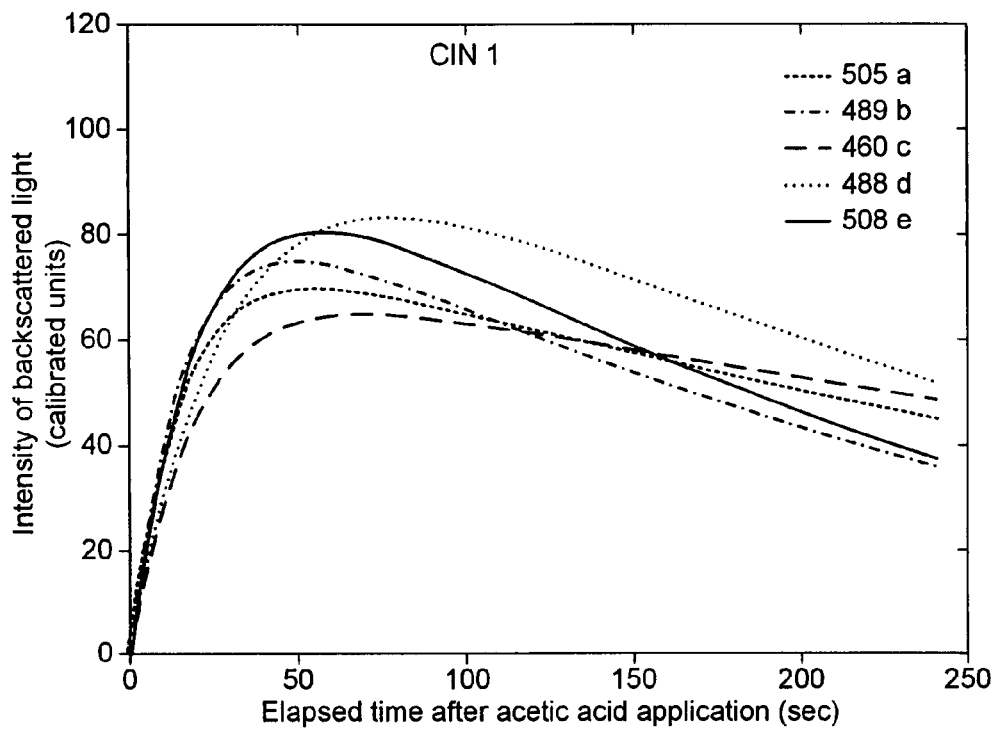
FIG. 4 shows exemplary DOCs obtained from cervical tissue sites interacting with acetic acid, corresponding to Cervical Intraepithelial Neoplasia I (CIN I), as classified by histology.

In particular, FIG. 2 demonstrates that the HPV-classified DOCs increase almost exponentially before reaching a saturation level, whereas the curves corresponding to inflammation reach a higher peak value earlier, and then decay abruptly as can be seen in FIG. 3. CIN1-classified curves, shown in FIG. 4, reach their maximum later than the curves corresponding to HPV or inflammation, and then decay with a slow rate that is notably slower than that observed in the inflammation cases. For the HG lesions shown in FIG. 5, the maximum of the curves is reached later and with a higher value than that observed in the HPV and CIN1 cases. However the decay rate for DOCs from HG lesions is very small; much smaller than that seen in the inflammation-classified curves. Although helpful, the previous description of the DOCs in relation to a specific pathological condition is rather qualitative. Hence, the following sections describe the quantitative parameters extracted from the dynamic optical curves which are able to discriminate robustly LG from HG lesions, and HPV infections from HG lesions.

Exemplary methods of the present invention include processing the DOC obtained from the tissue using mathematical formulations, including, but not limited to, polynomial, single-, bi-, and multi-exponential fitting, linear and non-linear decomposition, or combinations thereof, in order to derive a single, or combination of, DOPs depicting various characteristics of the recorded DOC in relation to a pathological condition.

According to aspects of the present invention, the derived DOPs can be weighted based on features particular to the tissue sample examined, such as, for example, patient age, menopausal period (for women), weighted based on features characterizing the regional, global, population of the subject whose tissue is examined, or both.

Figure 6:
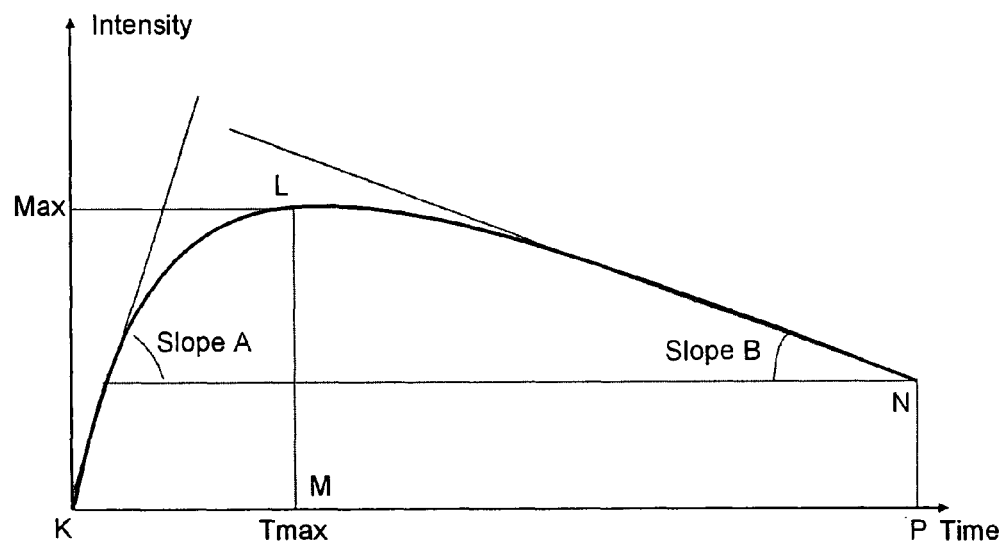
FIG. 6 illustrates the DOPs corresponding to an exemplary DOC, which may be used for diagnosing various pathological conditions of the tissue.

FIG. 6 illustrates six DOPs, each having a high diagnostic value in discriminating LG from HG lesions, on an idealized curve. These DOPs include:

1. Max

The 'Max' parameter is defined as the difference between maximum value of the recorded DOC (point L on the curve), after the application of a biomarker, and the DOC value at $t=0$ 2. Integral The 'Integral' parameter is defined as the area surrounded by the recorded DOC, and the line parallel to the time axis that intersects the first DOC experimental point (the area enclosed by the indicated points KLNP). The integral is calculated for a predetermined time period, which depends on the time duration of optical effects generated by the biomarker-tissue interaction. In the case of cervical tissue and acetic acid solution (biomarker) the integral is taken for $t=0$ to $t=4$ min. The 'Integral' parameter can be also calculated analytically through the integral of a mathematical formula, after approximation of the measured curve with a closed mathematical form.

3. Tmax

The 'Tmax' parameter is defined as the time required for reaching the maximum of the DOC (point L on the curve), where said maximum is the Max parameter.

4. Area to Max

This parameter is defined as the area of the curve corresponding to the DOC from $t=0$ sec (i.e., initialization time of the acetowhitening phenomenon), until $t=Tmax$ (the area enclosed by the indicated points KLM). Again, this parameter can also be calculated analytically through the integral of a mathematical formula, after approximation of the measured curve with a closed mathematical form.

5. SlopeA

This is a parameter expressing the rate of intensity increase until the 'Max' value. Indicatively, it can be calculated as the derivative of the first portion of the curve, or as the average of the intermediate slopes until the 'Max' value is reached.

6. SlopeB

This is a parameter expressing the rate of intensity decrease starting from the 'Max' value of the curve. Indicatively, it can be calculated as the derivative of the last portion of the curve or as the average of the intermediate slopes, starting from the 'Max' value.

Results appearing in FIGS. 7 to 10B, Table 1 and Table 2 are obtained from cervical epithelia in vivo, interacting with a 3% acetic acid solution as a biomarker in a clinical setting. The results are based on measurements of 308 women of the 447 women enrolled in the clinical trial. Histology using a tissue sample was used as a gold standard for determining a pathological condition for each tissue characterized.

Figure 7:
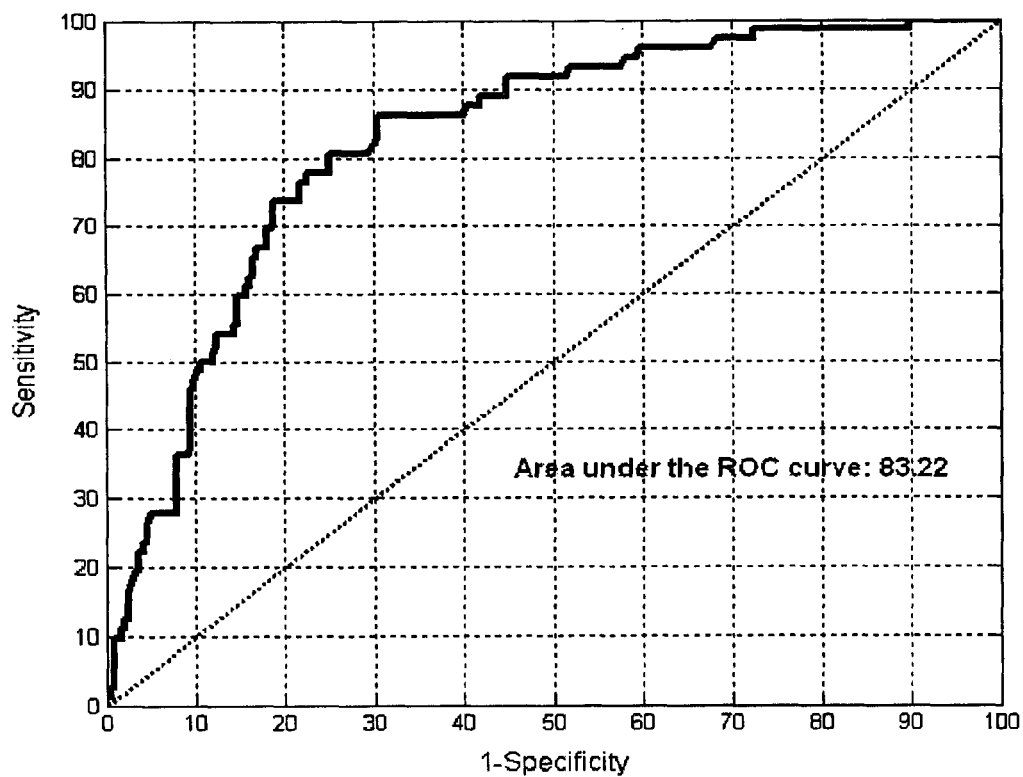
FIG. 7 illustrates the Receiver Operator Characteristics (ROC) curve corresponding to an indicative DOP (Integral) and the 'area under the ROC curve', expressing the performance of this particular DOP in discriminating low- from high-grade CIN. The results have been obtained from cervical epithelia in vivo, interacting with acetic acid solution, in a clinical setting where suitable measurements were conducted on 308 women of 477 women enrolled in a clinical trial.

FIG. 7 illustrates the LG/HG ROC analysis of the cumulative results for the 'Integral' parameter described previously. The area under the ROC curve is 0.83, implying high discrimination capability between an HG and a non-HG lesion. The best possible prediction of the method would yield a point in the upper left corner or coordinate (0,100) of the ROC space, representing 100% sensitivity (all true positives are found) and 100% specificity (no false positives are found). The (0,100) point is also called a perfect classification. A completely random guess would give a point along a diagonal line (the so-called line of no-discrimination) from the left bottom to the top right corners. The diagonal line divides the ROC space in areas of good or bad classification/diagnostic. Points above the diagonal line indicate good classification results, while points below the line indicate bad results.

Figure 8:
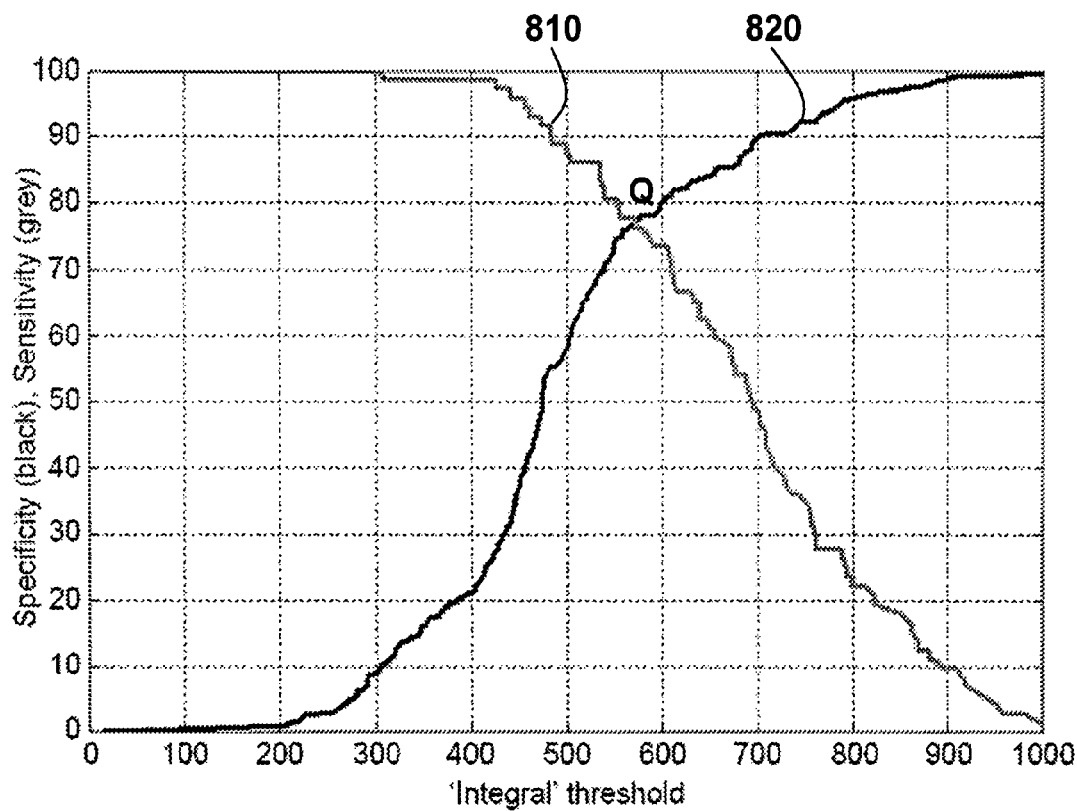
FIG. 8 shows the sensitivity (grey) and specificity (black) plots derived from ROC analysis corresponding to an indicative DOP (Integral), expressing the performance of this particular DOP in discriminating low-grade from high-grade lesions. An 'Integral' cut-off value selected from the range of about 480 to about 650 a.u. can be used for discriminating Low from High Grade cervical neoplasias with both SS and SP being greater than 60%. The results have been obtained from cervical epithelia in vivo, interacting with acetic acid solution 3%, in a clinical setting where measurements were conducted on 308 women.

FIG. 8 illustrates the sensitivity 810 (grey) and specificity 820 (black) plots derived from the ROC analysis for various values of the 'Integral' parameter used for the quantification of the acetowhitening characteristics. It is seen that for a certain value both sensitivity and specificity are maximized reaching 78%.

Figure 9A:
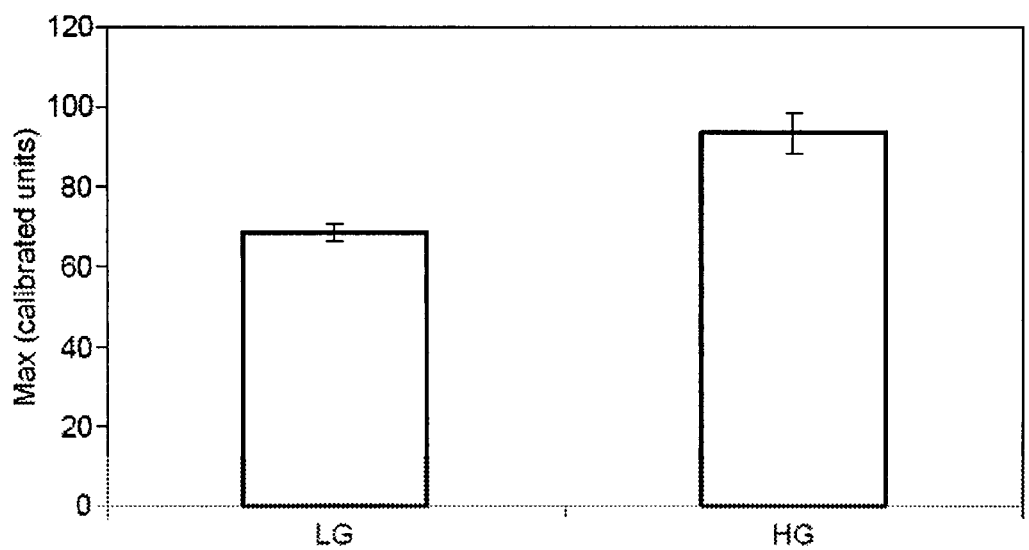
FIGS. 9A-E show the mean values, with corresponding error-bars, for five different DOPs extracted from the DOC. The results have been obtained from cervical epithelia in vivo, interacting with acetic acid solution, in a clinical setting where measurements were conducted on 308 women.
Figure 9B:
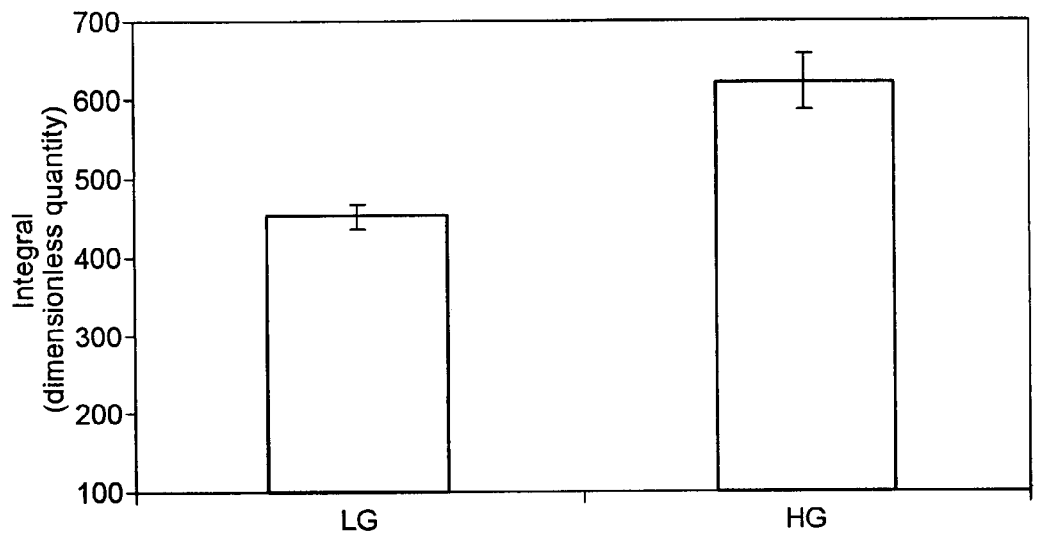
Figure 9C:
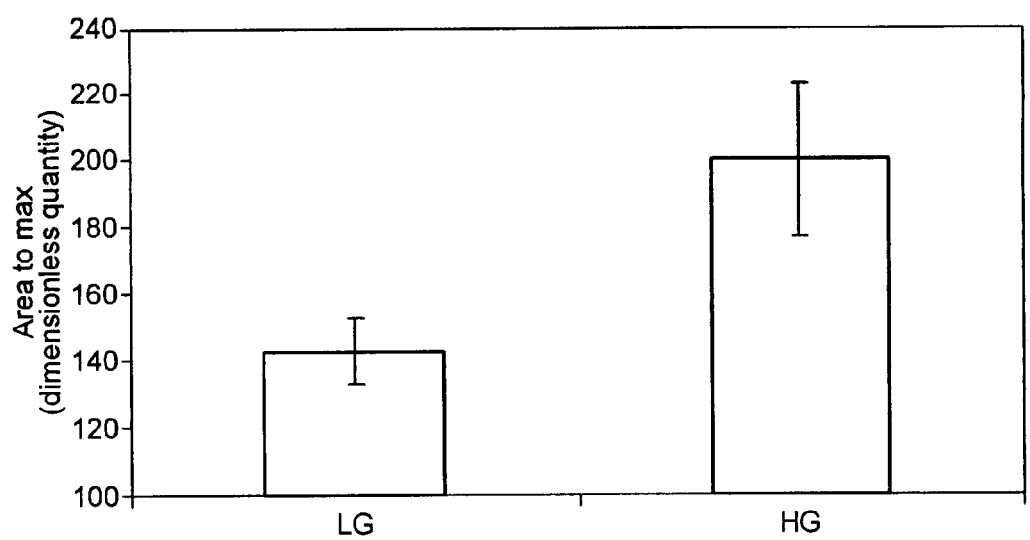
Figure 9D:
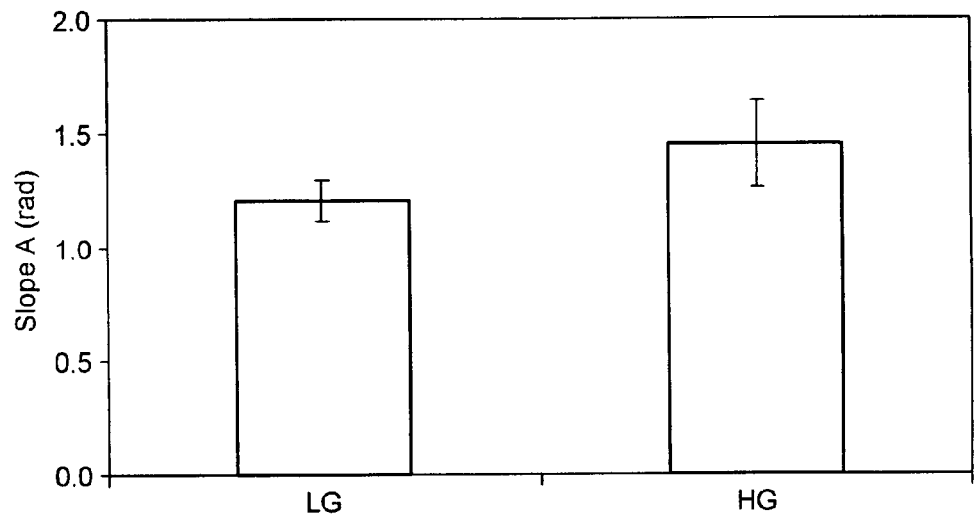
Figure 9E:
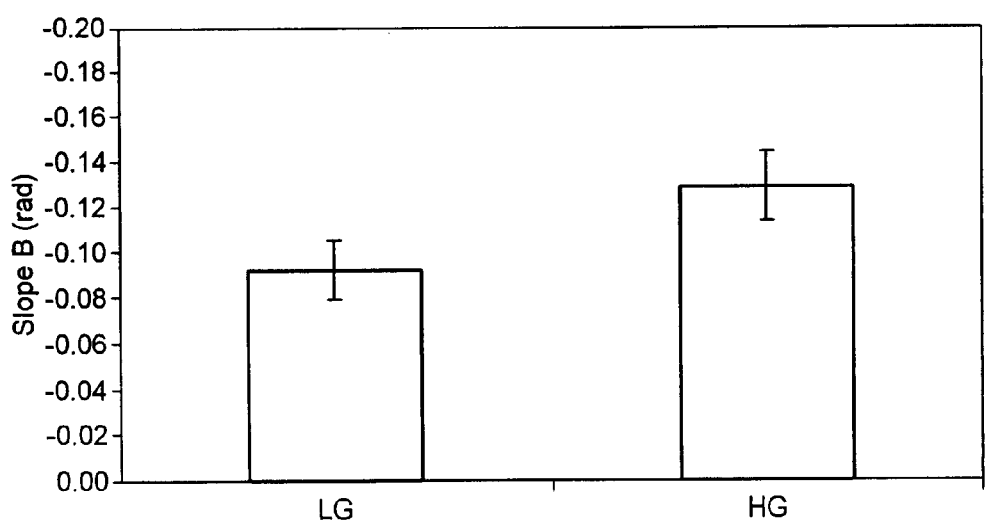

FIG. 9A to 9E graphically depicts the mean values, with corresponding error-bars representing 95% confidence intervals, for some of the parameters described previously, for the LG and HG diagnostic conditions, as concluded through biopsy examination performed by the histologists FIG. 9A depicts a mean value of the Max for LG tissues and for HG tissues, and shows the mean Max value for the HG tissues larger than the mean Max value for LG tissues. FIG. 9B depicts a mean value of the Integral for LG tissues and for HG tissues, and shows the mean Integral value for HG tissues larger than the mean Integral value for LG tissues. FIG. 9C depicts a mean value of the 'Area to Max' for LG tissues and for HG tissues, and shows the mean 'Area to Max' value for HG tissues larger than the mean 'Area to Max' value for LG tissues. FIG. 9D depicts a mean value of the SlopeA for LG tissues and for HG tissues, and shows the mean SlopeA value for HG tissues larger than the mean SlopeA value for LG tissues. FIG. 9E depicts a mean value of the SlopeB for LG tissues and for HG tissues, and shows the mean SlopeB value for HG tissues more negative than the mean SlopeB value for LG tissues.

The optimum value ranges in discriminating LG from HG lesions were calculated with ROC analysis, as shown previously for the 'Integral' parameter. In particular, for each parameter type the percentage of true positives (TP) and false positives (FP) was calculated for various threshold values spanning the entire range: [Pmin, Pmax], where P denotes the value of a specific parameter. The threshold value where the sensitivity (SS=TP), and specificity (SP=100−FP), approximately coincide with one another was used as an optimum (cut-off) value for discriminating LG from HG.

TABLE 1 illustrates the optimum value ranges for discriminating LG from HG lesions for some of the defined parameters, leading to a performance dictated by specificity and sensitivity greater than 60%.

TABLE 1

| Parameter | Optimum parameter cut-off values for LG/HG discrimination |
|---|---|
| ΔMax* | 70 to 90 (calibrated units) or 15-25% (reflectance) |
| Integral** | 480 to 650 (dimensionless quantity) |
| Time-to-max | 80-100 sec |
| Area to Max** | 120 to 170 (dimensionless quantity) |
| SlopeA | 1.1 to 1.3 (rad) |
| SlopeB | −0.012 to −0.090 (rad) |

*The parameters listed above have been obtained with a color imaging system calibrated against a 18% reflecting calibration specimen to produce for the latter a gray value of 105 in a 0-255 gray scale in the green channel of the system. Based on this calibration protocol Max is given as green gray value max difference in calibrated units (scale 0-255) or as reflectance max difference (scale 0-100%)
**The presented integral cut-off values have been calculated from a DOC corresponding to a τ = 240 sec integration time:

$$Itg = c \int_0^{240} (I_t - I_{t=0}) dt \quad \text{(Equation 1)}$$

Where c is a scaling factor with value $c=8[\tau I_{t=0}]^{-1}$ or by substituting $c=1/30$ (intensity units)$^{-1}$ sec$^{-1}$, $I_{t=0}$ the remitted intensity at a given time point after the application of the biomarker, and $I_0$ the remitted intensity before the application of the biomarker. Accordingly, Area to max is calculated from the same with Itg formula and the only difference is that τ=Tmax. Both Itg and Area-to-Max are presented here as dimensionless quantities Different acquisition, integration time periods and calibration protocols and samples may result in different cut-off values. The 250 sec integration time period is selected as an optimum time period for a particular tissue type and a particular biomarker and it is presented here as an example and not as a restriction. For example integration time of about 120 sec could also provide meaningful results while in parallel shortening the examination time.

One of ordinary skill in the art will appreciate that the integral may be calculated over a different (longer or shorter) integration time that would necessitate rescaling the cut-off value of the "Integral" accordingly. Additionally, one of ordinary skill in the art will appreciate that defining the calibration units in a different manner may necessitate appropriately rescaling cut-off values for ΔMax, Integral, Area to Max, SlopeA and SlopeB.

Although aspects and features of embodiments of the present invention have been shown and described with reference to specific embodiments, those skilled in the art will understand that variations in the form and detail may be made without departing from the spirit and the scope of the invention As demonstrated by FIG. 9B, an 'Integral' value greater than a cut-off value indicates the presence of an HG lesion, according to aspects of the present invention. Based on the analysis described above with the requirement that both specificity and sensitivity are greater than 60%, and based on the data presented, the 'Integral' parameter of the DOC may have a cut-off value between about 480 and about 650.

As demonstrated by FIG. 9A, a 'Max' value greater than a cut-off value indicates the presence of an HG lesion, according to aspects of the present invention. Based on the analysis described above with the requirement that both specificity and sensitivity are greater than 60%, and based on the data presented, the 'Max' parameter of the DOC may have a cut-off value of between about 70 and about 90 for discriminating between an HG lesion and an LG lesion.

According to further aspects of the present invention, a 'time to Max' ('Tmax') value greater than a cut-off value indicates the presence of an HG lesion. Based on the data presented, the 'time to Max' ('Tmax') parameter may have a cut-off value between about 80 and about 100 secs for discriminating LG from HG lesions.

As demonstrated by FIG. 9C, an 'Area to Max' ('Tmax') value greater than a cut-off value indicates the presence of an HG lesion, according to aspects of the present invention. An 'Area to Max' parameter with a cut-off value of between about 120 and about 170 may be used for discriminating LG from HG lesions.

As demonstrated by FIG. 9D, a SlopeA value greater than a cut-off value indicates the presence of an HG lesion, according to aspects of the present invention. The 'SlopeA' parameter with a cut-off value of between about 1.1 and about 1.3 may be used for discriminating LG from HG lesions.

As demonstrated by FIG. 9E, a SlopeB value smaller (more negative) than a cut-off value indicates the presence of an HG lesion, according to aspects of the present invention. The 'SlopeB' parameter with a cut-off value of between about −0.012 and about −0.090 may be used for discriminating LG from HG lesions.

A similar analysis was performed for deriving the appropriate cut-off values of the previous parameters for discriminating HPV infections from HG lesions.

TABLE 2 illustrates the optimum value ranges generating specificity and sensitivity greater than 60% for HPV/HG discrimination, for the 'Max' and 'Integral' parameters.

TABLE 2

| Parameter | Optimum parameter cut-off values for HPV/HG discrimination |
|---|---|
| Max | 65 to 90 (calibrated units.) |
| Integral | 380 to 490 (dimensionless units) |

In a preferred embodiment, the 'Integral' parameter of the DOC with a cut-off value of between about 380 and about 490 is used for discriminating HPV infections from HG lesions. An 'Integral' value less than a cut-off value indicates the presence of an HPV infection.

In another embodiment the 'Max' parameter of the DOC with a cut-off value of between about 65 and about 90 is used for discriminating HPV infections from HG lesions. A 'Max' value less than said cut-off value indicates the presence of an HPV infection.

In yet another embodiment, combinations of parameters including but not limited to the above mentioned may provide a means for determining the pathology of tissue. For example, such a parameter may be the product of the average slope DOC until about 40 sec sampling time after the application of said biomarker, by the Max value. Product values greater than about 2.05±0.2 (calibrated intensity units/time) may indicate the presence of high grade neoplasia, whereas lower values may indicate low grade neoplasia or healthy tissue.

Beyond the 'hard-clustering' approach using a cut-off parameter value for discriminating LG from HG lesions, or HPV from HG lesions, more advanced statistical and pattern recognition analysis techniques (such as Bayesian classification, Artificial Neural Networks (ANNs), classification trees), may be employed to extract other linear, or non-linear, of single or combinations of multiple, parameters for achieving high discrimination. In yet another embodiment, a parametric approach, using Bayesian modelling (as described in, for example, Fukunaga K. (1990) *New York: Academic*, $2^{nd}$ Ed.), and a non-parametric approach, using ANNs (Learning Vector Quantization-LVQ, see as described in, for example, Kohonen T., (1986) *Int. J. Quant. Chem.*, Suppl. 13, 209-21), were employed for differentiating the DOPs obtained from corresponding DOC of tissue sites with LG and HG neoplasia. For both Bayes and NN classification, the overall discrimination performance of LG and HG lesions was greater than 75%, for various combinations of the optical parameters described previously, and for a variable number of training sets selected from the overall sample.

Another embodiment includes a means for automated cervical screening through the mapping of the dynamic parameter values, and the corresponding cut-off values, showing presence of the disease.

A different embodiment includes a means for semi-automated colposcopy through the mapping of the dynamic parameter values and corresponding cut-off values showing presence of the disease. Such a methodology ensures a baseline colposcopy performance independently of the practitioner's skills, facilitating the overall diagnostic procedure, follow-up, and guidance during biopsy sampling and treatment.

Yet another embodiment includes the interpretation of the acetowhitening phenomenon dictated by the dynamic parameters in relation to the functional and structural alterations in the epithelium. In one embodiment, distinctive parameters related to the cervical tissue structural properties are computed and correlated with a number of functional features derived from the DOC recorded from the same tissue sites. Specifically, there is a common agreement in terms of the direct correlation between the nuclear volume and grading of neoplasia (HPV, CIN1, CIN2 and CIN3), or cervical cancer [Walker D C, et al. (2003) *Physiological Measurement*, 24:1-15]. The nuclear-to-cytoplasmic-ratio (NCR), which expresses the nuclear density in the epithelial tissue, is the most common parameter used to describe this correlation with certain diagnostic conditions. In one embodiment, the cellular structure of the tissue is assessed by finding the correlation formula between either, or combination, of the aforementioned dynamic parameters with the NCR computed from the biopsy material extracted from corresponding cervical locations. To this end, the NCR was correlated with the DOC parameters reflecting the abnormal functioning of the epithelium, after acetic acid induction into the tissue area.

In yet another embodiment, this correlation could lead to the extraction of a pseudocolor map representing the structural properties of the examined cervical tissue at every location, in addition to the map representing the acetowhitening kinetic characteristics, along with highlighted sites of high nuclear density. Such an implementation has an exceptional value if one thinks that by quantifying the in vivo optical curve obtained from the tissue, which represents an in vivo assessment of the macro-structural tissue state; one can also derive direct conclusions about the cellular properties of the tissue, which constitutes a representative view of its structure at a microscopic level.

In order to calculate the NCR for a corresponding number of epithelial tissue sites from which the dynamic parameters were obtained by the methods disclosed herein, an equal number of cervical biopsy samples were obtained during colposcopy. The biopsied tissue was processed through standard procedures, immunohistochemically stained, and placed on slides for further evaluation through microscopic image analysis. After acquiring an equivalent number of microscopic histological images, a multistage image-analysis algorithm was employed for segmenting the cell-nuclei displayed in the images [Loukas C G, et al. (2003) Cytometry, 55A(1): 30-42]. The NCR quantity was calculated as the sum of the area occupied by the nuclei enclosed in the epithelium, divided by the overall area of the epithelial tissue. NCR is also known as the 'cell-packing' property of the epithelial tissue, expressing essentially the cross-sectional structure of the tissue's cellular population.

Figure 10A:
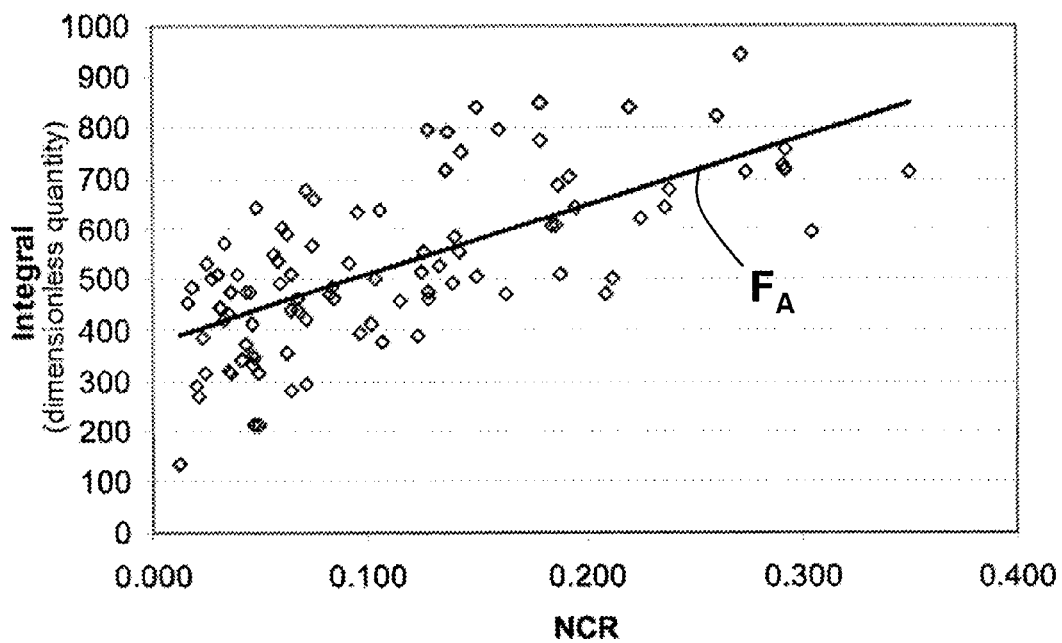
FIGS. 10A and 10B show scatter plots and linear regression curves of nuclear-to-cytoplasmic-ratio (NCR), assessed quantitatively in tissue samples against two different DOPs (Integral and Max) obtained from the same samples before biopsy. The results have been obtained from cervical epithelia in vivo, interacting with acetic acid solution, in a clinical setting where measurements were conducted on 308 women.
Figure 10B:
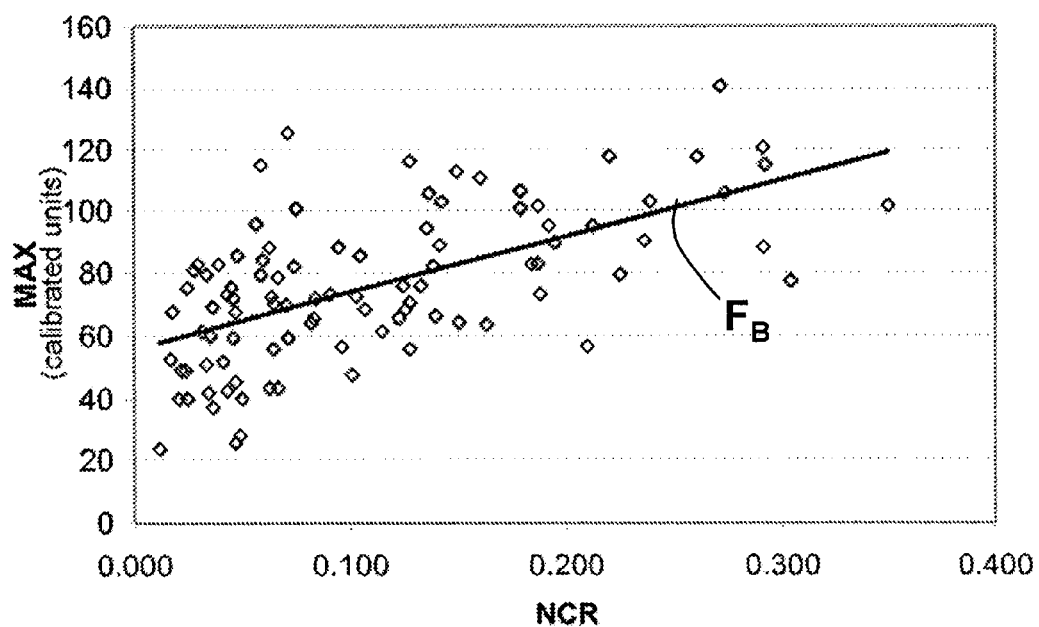

In an illustrative embodiment, FIG. 10A and FIG. 10B show scatter plots of two different DOPs exhibiting the strongest correlation coefficient (R), against NCR. These parameters are the 'Integral', and the maximum value (Max), of the dynamic optical curve, as defined previously. The lines in the graphs $F_I$ and $F_M$ represent linear regression curves, whereas the DOP to NCR conversion equation and correlation results obtained from least-squares fitting on the experimental data are shown in TABLE 3.

TABLE 3

| NCR vs DOP | Correlation Coefficient | Conversion Equation |
| --- | --- | --- |
| NCR vs 'Integral' Fit $F_1$ | 0.71 | $NCR = \frac{1}{1349} \times Integral - 0.278$ |
| NCR vs 'Max' Fit $F_M$ | 0.64 | $NCR = \frac{1}{181} \times Max - 0.309$ |

From this table it can be seen that both parameters present a significant correlation with the cell-packing property of the tissue. In one embodiment of the method, the linear equations allow conversion of a DOP corresponding to a DOC obtained from a specific tissue site, to the underlying NCR property of the tissue site.

In another embodiment of the method, either of the quantitative pseudocolor maps of 'Integral', or 'Max', can be converted to the NCR map of the epithelial tissue, using the previously shown conversion formulas.

In addition to the structural alterations of the epithelial tissue in relation to neoplasia progression, there are also several functional changes in the extracellular and intracellular space of the epithelium after applying the acetic acid solution. In particular, solid tumours are known to live in an acidic microenvironment [Webb S D, at al. (1999) *J. Theor. Biol.*, 196: 237-250; Lee A H, et al. (1998) *Cancer Research*, 58: 1901-1908; Yamagata M et al. (1996) *Br. J. Cancer*, 73: 1328-1334; and Marion S, et al. (2000) *Molecular Medicine Today*, 6: 15-19]. Besides, experimental measurements have shown that extracellular pH in tumors is on average 0.5 units lower than that of normal tissues, with tumor extracellular pH lying typically in the range [6.6, 7.0] (see [Yamagata M et al. (1996) *Br. J. Cancer*, 73: 1328-1334]). Tumor cells also have a neutral or slightly alkaline intracellular pH [Marion S, et al. (2000) *Molecular Medicine Today*, 6: 15-19]. Similar to the normal cells, tumor cells regulate their cytoplasmic pH within a narrow range to provide a favorable environment for various intracellular activities.

Although the issue regarding the presence of acidic extracellular pH in tumors is still controversial, there is a common belief that the acidic environment of tumors arises from the high rate of metabolic acid production, such as lactic acid, and from its inefficient removal from the extracellular space [Webb S D, at al. (1999) *J. Theor. Biol.*, 196: 237-250; Lee A H, et al. (1998) *Cancer Research*, 58: 1901-1908; Marion S, et al. (2000) *Molecular Medicine Today*, 6: 15-19; and Prescott D M, et al. (2000) *Clinical Cancer Research*, 6;(6): 2501-2505]. Besides, tumor cells have a high rate of glycolysis, regardless of their oxygen supply level. As a consequence, large quantities of lactic acid (and subsequently $H^+$) are produced outwards from the cellular environment. Due to a number of factors such as a disorganized vasculature, or poor lymphatic drainage, and elevated interstitial pressure, the acid clearance ($H^+$ clearance) to the blood is very slow, and thus a reversed pH gradient between the extracellular and the intracellular space of tumors cells is observed, [Webb S D, at al. (1999) *J. Theor. Biol.*, 196: 237-250; Lee A H, et al. (1998) *Cancer Research*, 58: 1901-1908; Yamagata M et al. (1996) *Br. J. Cancer*, 73: 1328-1334; and Marion S, et al. (2000) *Molecular Medicine Today*, 6: 15-19]. It is also reasonable to assume that the CIN extracellular environment is also acidic (perhaps less acidic), provided that cancer is a transitional process and CIN is a precursor of cancer. Moreover, tumor as well as dysplastic cells are known to employ the same short-term, [Marion S, et al. (2000) *Molecular Medicine Today*, 6: 15-19], and long-term [Lee A H, et al. (1998) *Cancer Research*, 58: 1901-1908; Yamagata M et al. (1996) *Br. J. Cancer*, 73: 1328-1334 and Prescott D M, et al. (2000) *Clinical Cancer Research*, 6;(6): 2501-2505], pH regulation mechanisms as those of normal cells. The excess of protons produced by tumor cell metabolism is excreted from the cell via specific hydrogen pumps [Prescott D M, et al. (2000) *Clinical Cancer Research*, 6;(6): 2501-2505].

The observation of the acetowhitening effect in the cervix is used in colposcopy to characterize abnormal tissue (i.e. HPV, CIN, or cancer). The acetowhitening effect refers to the phenomenon induced by the application of acetic acid solution to the cervical transformation zone. The acetic acid application selectively induces a transient whitening of abnormal cervical areas. Although it has been used for more than 70 years in clinical practice to locate abnormal areas, the exact physicochemical mechanisms involved in tissue whitening remain still unknown. Similar phenomena are observed when Formic, Propionic, and Butyric, acids are employed as biomarkers.

Two major explanations for the interpretation of the acetowhitening effect prevail in the relative literature. In vitro studies have shown that the acetic acid effect is related to the amount of certain cytokeratines (proteins present in epithelial cells) [Maddox P, et al. (1999) *Journal of Clinical Pathology*, 52: 41-46 and Carrilho C, et al. (2004) *Human Pathology*, 35: 546-551]. Since in cervical neoplasias the extra-cellular environment is acidic, the topically administered acidic acid molecule is not disassociated to its composing ions and as such can penetrate passively the cell membrane. Entering into the neutral pH cytoplasm the acetic acid molecules are disassociated giving hydrogen and carboxylic ions which interact with nuclear proteins resulting in the alteration of the scattering properties of the abnormal cells selectively.

Cytosolic pH value is crucial for the conformational stability of these proteins. At neutral pH values, proteins are stable in solution. As pH drops, they become unstable and insoluble depending on their pI (isoelectrical point). The process of protein destabilization is called denaturation and this partial denaturation is a reversible process which lasts only for some milliseconds. Denatured or unfolded proteins have a different refractive index, and this may be the reason for the whitening effect. The decrease of pH in normal cells may not be enough to cause the proteins to unfold and perhaps this is the reason that in normal tissue no variation in the IBSL is detected. Thus, the back-scattered light is strongly related to the pH dynamics influenced by the acetic acid penetration in the cervical epithelium. Nevertheless, the proteins that contribute to the effect are not well established. Moreover, each of these proteins may denature at a different pH value.

According to the other interpretation, the action of acetic acid on the epithelium of the transformation zone is related to its concentration [MacLean A B. (2004) *Gynecologic Oncology*, 95: 691-694]. Acetic acid enters in the cellular environment of the dysplastic layers altering the structure of different nucleoproteins and hence causing the cells to appear opaque. Thus, the dynamics of the back-scattered light follows the dynamics of the acetic acid concentration. In normal tissue, no whitening occurs because the quantity of nucleoprotein is very small.

Based on the above mentioned analysis of the functional and structural features of the epithelium undergoing changes during neoplasia development it is possible to correlate dynamic optical data with epithelial features of diagnostic importance. In particular, the measured dynamic characteristics can be used to decouple various epithelial structural and transport phenomena occurring in time sequence after the application of the biomarker, and to correlate them with in vivo measurable optical parameters thus providing a solution to the inverse problem. In other words, it is possible to obtain information for various epithelial features by measuring in vivo dynamic characteristics and parameters.

In one embodiment of the method, 'SlopeA' is used to obtain information for the extracellular acidity, and in turn for the passive diffusion constant, and for the number of cell layers of the stratified epithelium. In another embodiment of the method, 'Max' is used to determine the NCR of the epithelium since the intensity of the back-scattered light is proportional to the density of signal sources (cell nuclei). In another embodiment of the method, 'SlopeB' is used to obtain information in regard to the cell malfunction in regulating the intracellular pH, and to the existence of disorganized vasculature, or to the poor lymphatic drainage associated with neoplasia development. In another embodiment, the 'Integral' parameter is used to obtain combined information for both functional and structural features as described above.

Clinical validation of this biophysical model has been performed by correlating NCR with the 'Max' and 'Integral' parameters described previously. However, clinical validation of the functional features is clinically impracticable due to the lack of reference methods capable of measuring these features in vivo. In contrast, methods disclosed herein are capable of modelling and predicting in vivo functional characteristics of the tissue, based on their capability of recording, analysing, and displaying dynamic optical characteristics obtained in vivo from a tissue interacting with a biomarker, and the ability to relate said optical characteristics of tissue with functional characteristics through modelling.

Figure 12:
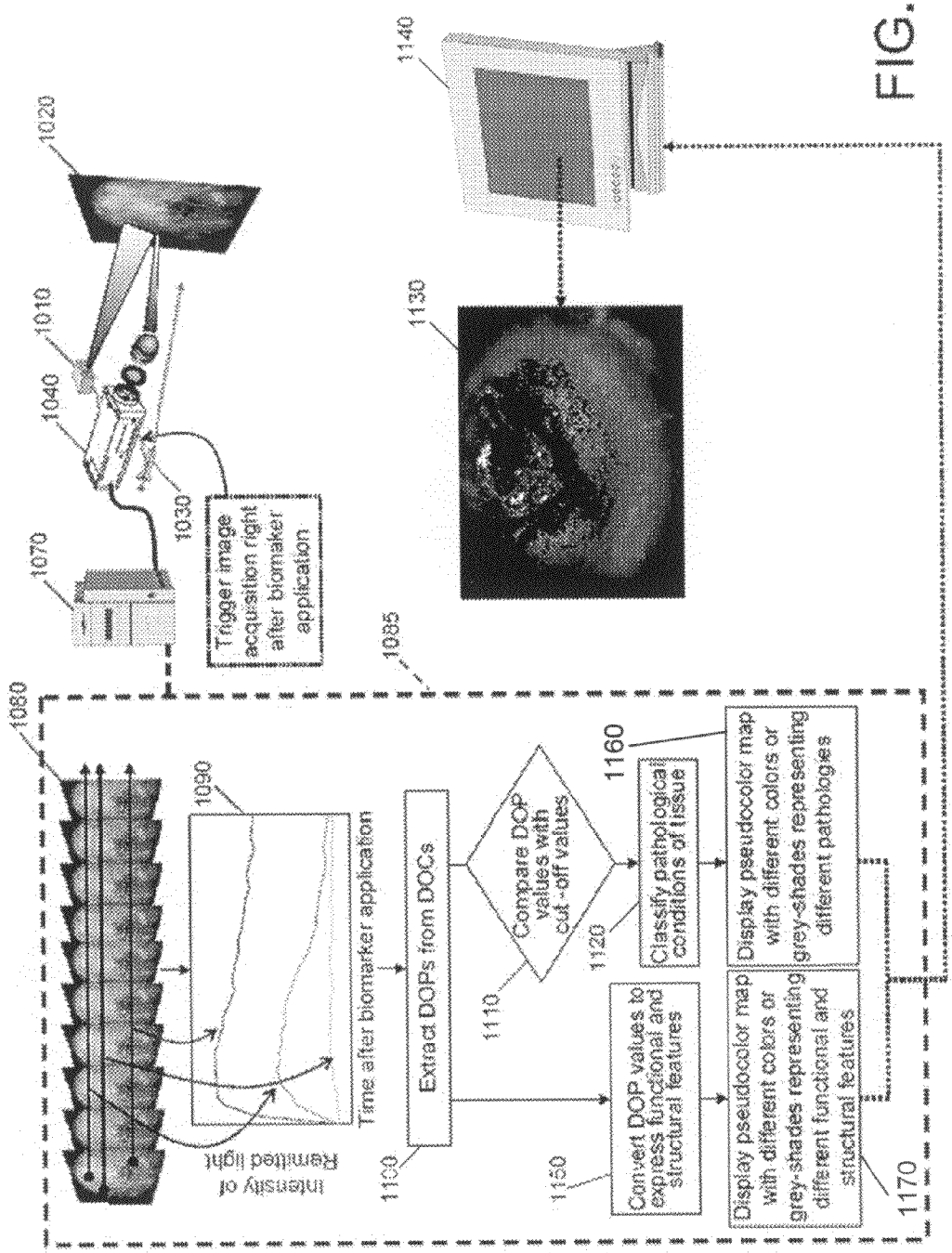
FIG. 12 shows the steps followed by a software implementation of the invention disclosed herein in connection with an exemplary embodiment of the hardware setup utilized to acquire the image tissue data.

FIG. 12 depicts another illustrative embodiment of the present invention. Computing device 1070 executes instructions embodied on a computer readable medium defining at least a processing procedure 1085. The computing device 1070 may also be connected with a hardware set-up utilized to obtain the tissue image data. In particular, the tissue 1020, is constantly illuminated with a light source 1010. After application of a suitable biomarker by means of an applicator 1030, a trigger signal is provided to initiate image acquisition using an image acquisition device 1040 such as a video CCD or other suitable image acquisition device. Between the tissue 1020 and the image acquisition device 1040 are one or more optical filters 1050 and lenses 1060, for example, one or more zoomable lenses can be interposed. The optical filter 1050 can be tuned to a preferred spectral band, at which maximum contrast is obtained between areas that are subjected to different grade of alterations in their optical reflectance or fluorescence characteristics after administering an appropriate agent.

Before agent administration, a tissue image is obtained as a reference. After agent administration, a series of images 1080, in time succession at the same or different time steps, at predetermined spectral bands, and for a predetermined time period, is obtained and stored in memory or a storage device internal to or external to the computing device 1070, for further processing by the image processing engine 1085. After proper alignment of some or all of the acquired images, a DOC 1090 is generated for each specific image location corresponding to the same tissue point in all of the images. In step 1100, one or more dynamic optical parameters expressing the dynamic characteristics of the phenomenon are derived from the DOCs, (step 1100).

The values of the extracted DOPS can be compared with reference values (such as predetermined cut-off values) to classify various pathological conditions of the tissue (step 1120). A resulting pseudolor map 1130, can then be displayed on a display device 1140, with different colors, or grey-shades, representing different pathologies, (step 1160). Alternatively, the classification of the various pathological conditions of the tissue can be stored for display at another time or sent to another computing device by, for example, a packet or other unit suitable for use in transporting data in a network environment.

Alternatively, in step 1150, the DOP values can be converted using predetermined mathematical formulas, to express functional and structural features of the tissue, (step 1170). In this case, a pseudolor map 1130, can be displayed on the display device 1140 with different colors, or grey-shades, representing different functional and structural features.

Figures 13A, 13B:
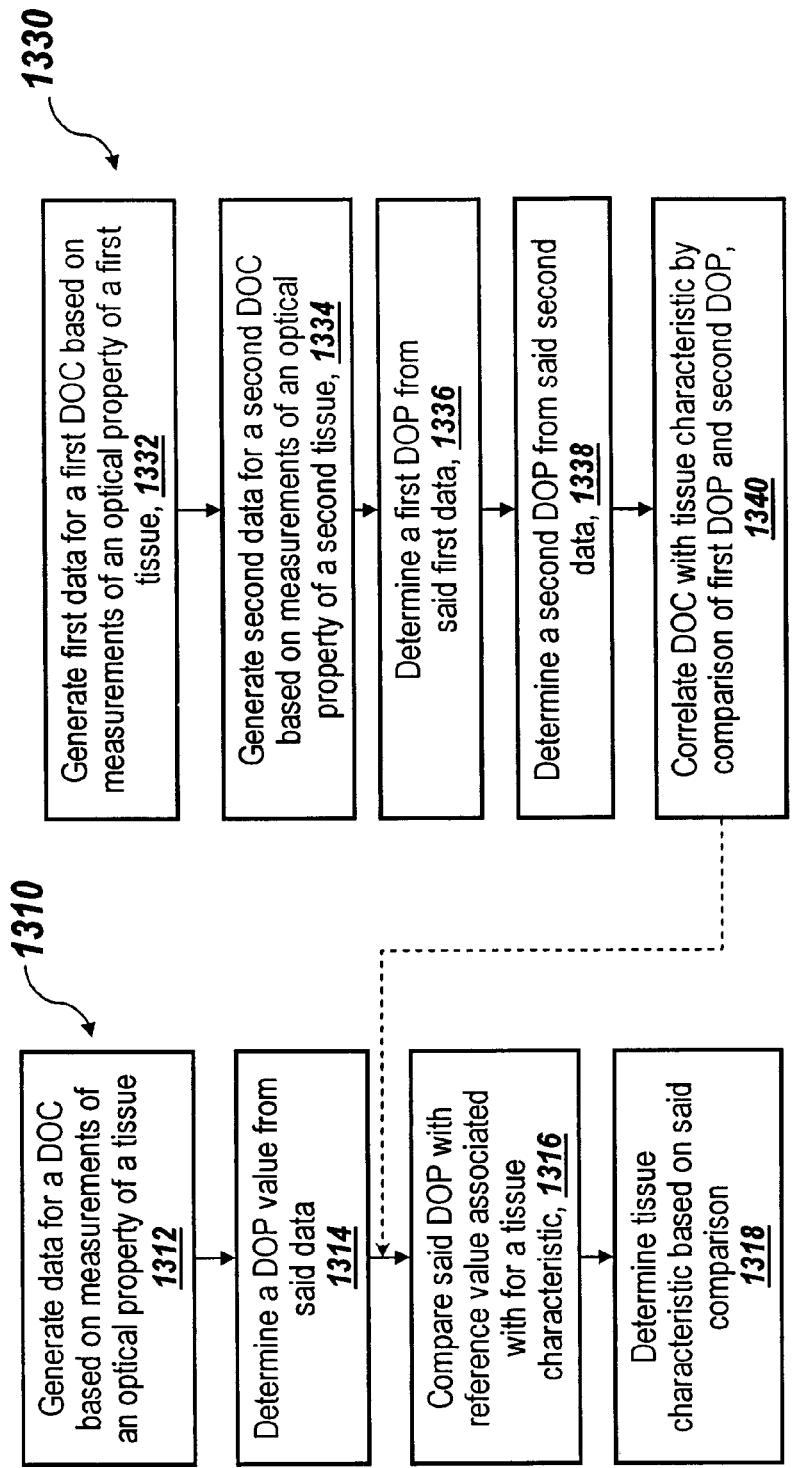
FIG. 13A is a flow chart of another method for determining tissue characteristics in accordance with one embodiment of the present invention.
FIG. 13B is a flow chart of a quantitative method for determining dynamic optical parameters useful for determining tissue characteristics, in accordance with one embodiment of the present invention.

Additional, exemplary methods that are embodiments of the present invention are depicted in FIGS. 13A to 13B. A quantitative method 1310 for determining tissue characteristics is depicted in FIG. 13A. Data is generated for a dynamic optical curve (DOC) based on measurements of an optical property of a tissue, or portion thereof, that has been exposed to a biomarker (step 1312). Generation of data for the dynamic optical curve (DOC) may include aligning image captures of the tissues. The generated data is used to determine a value of a dynamic optical parameter (DOP) (e.g. 'Integral', 'Tmax', etc.) (step 1314). The value of the DOP is compared with at least one reference value of the DOP that is known to be linked to a tissue characteristic (step 1316). Based on the comparison a tissue characteristic is determined for the tissue (step 1318). The tissue characteristic may be a structural characteristic, a functional characteristic a pathological status of the tissue or a combination of any of the aforementioned. A tissue characteristic may be determined at a plurality of tissue locations on the tissue by conducting the aforementioned steps (step 1312 through step 1318) at each tissue location. Each tissue location identifies a portion of the tissue for which data is generated, a value of a dynamic optical parameter is determined and a characteristic is determined. A map of the tissue characteristic may be generated based on the tissue characteristic associated with each tissue location. Additionally, a map of values of the DOP for various tissue locations may be generated.

FIG. 13B depicts an quantitative method 1330 for determining one or more dynamic optical parameters useful for determining tissue characteristics. First data is generated for a first dynamic optical curve based on the variation of an optical property of a first tissue, or potion thereof (step 1332). The first tissue is known to have a particular tissue characteristic and has been exposed to a biomarker. Second data is generated for a second dynamic optical curve based on the variation of an optical property of a second tissue, or potion thereof (step 1334). The second tissue is known not to have a particular tissue characteristic and has been exposed to a biomarker. A first value of at least one dynamic optical parameter is determined from said first dynamic optical curve (step 1336) and a second value of at least one dynamic optical parameter is determined from said second optical curve (step 1338). At least one dynamic optical parameter is correlated with said particular tissue characteristic by comparison of said first value and said second value (step 1314).

According to aspects of the present invention, the steps for generating data for a first dynamic optical curve (step 1312), and determining said first value of at least one dynamic optical parameter (step 1316) may be repeated a number of times using a separate tissue sample known to have said particular tissue characteristic each time resulting in a group of first values. The steps for generating data for a second dynamic optical curve (step 1314), and determining said first value of at least one dynamic optical parameter (step 1318) may repeated a number of times using a separate tissue sample known to not to have said particular tissue characteristic each time resulting in a group of first values. The step of correlating the at least one dynamic optical parameter and said particular tissue characteristic (step 1340) may include comparing the group of first values and the group of second values to determine a reference value of said at least one dynamic optical parameter.

Any aspects of the methods depicted in FIGS. 13A and 13B may be combined with any other aspects of embodiments of the present invention described herein.

The contents of all references, figures, patents and published patent applications cited throughout this application are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims. Additionally, numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the illustrative embodiments may vary substantially without departing from the spirit of the invention, and exclusive use of all modifications that come within the scope of the appended claims is reserved. It is intended that the present invention be limited only to the extent required by the appended claims and the applicable rules of law.

The invention claimed is:

1. A quantitative method for determining a tissue condition, comprising:
    measuring, in vivo, temporal alterations of an optical property of a tissue at a plurality of spatial locations of the tissue, wherein the temporal alterations are provoked by application of a biomarker to the tissue;
    calculating a dynamic optical curve from the measured optical property data for each spatial location in the plurality of spatial locations;
    determining values of a set of dynamic optical parameters from the dynamic optical curve for each spatial location in the plurality of spatial locations; and
    determining a tissue condition using the determined values of the set of dynamic optical parameters and reference values for the set of dynamic optical parameters at each spatial location in the plurality of spatial locations; wherein the tissue is an epithelial tissue; and wherein the tissue condition is selected from the group consisting of normal tissue, cervical neoplasia, HPV infection, dysplasia, pathologic, cancerous and precancerous, wherein the set of reference values are determined by steps comprising:
    correlating values for a plurality of dynamic optical parameters of a reference tissue sample, obtained in vivo, with a diagnosis of a tissue condition of the reference tissue sample, obtained by an in vitro diagnostic test, for a statistically significant number of tissue samples; and
    determining, on the basis of said correlations, a set of dynamic optical parameters for discriminating between tissue conditions, a value range of each dynamic optical parameter in the set of dynamic optical parameters, and a cut-off value for each dynamic optical parameter in the set of dynamic optical parameters that discriminates between various conditions of tissue;
    wherein the cut-off values are reference values to discriminate between tissue conditions including normal, pathologic, and cancerous, and
    wherein the cut-off value of each dynamic optical parameter is such that the sensitivity and the specificity of the dynamic optical parameter are approximately the same.

2. The method of claim 1, further comprising the step of mapping and border-lining, in vivo, a tissue condition at each spatial location in the plurality of spatial locations by correlating a color at the spatial location with a dynamic optical parameter value range that includes a determined dynamic optical parameter value at the spatial location.

3. The method of claim 1, wherein the biomarker is a 3%-5% acetic acid solution; and wherein the dynamic curve is a dynamic scattering curve obtained during a time period after application of said biomarker.

4. The method of claim 1, wherein the set of dynamic optical parameters comprises an 'Integral' parameter that is an integral of a magnitude of the dynamic optical curve with respect to time over a predetermined time period; and
    wherein the reference values comprise:
        an upper 'Integral' cut-off value, wherein a determined 'Integral' value greater than the upper 'Integral' cut-off value indicates a high-grade neoplasia; and
        a lower 'Integral' cut-off value, wherein a determined 'Integral' value less than the lower 'Integral' cut-off value indicates an HPV infection.

5. The method of claim 1, wherein the set of dynamic optical parameters comprises a Max parameter that is a difference between a maximum value of a magnitude of the dynamic optical curve and a value of the dynamic optical curve before the biomarker is applied; and
    wherein the reference values comprise:
        an upper Max cut-off value, wherein a determined Max value greater than the upper Max cut-off value indicates a high-grade neoplasia; and
        a lower Max cut-off value, wherein a determined Max value less than the lower Max cutoff value indicates an HPV infection.

6. The method of claim 5, wherein the upper Max cut-off value is between about 70 and about 90; and wherein the lower Max cut-off value is between about 65 and about 90.

7. The method of claim 1, wherein the biomarker is a 3%-5% acetic acid solution; wherein the dynamic curve is a dynamic scattering curve obtained during a time period after application of said biomarker;
    wherein the set of dynamic optical parameters comprises a $T_{max}$ parameter that is a time required to reach a maximum value of the dynamic optical curve after application of the biomarker; and wherein the reference values comprise a $T_{max}$ cut-off value that is between about 80 seconds and about 100 seconds, and wherein a determined $T_{max}$ value greater than the $T_{max}$ cut-off value indicates a high-grade neoplasia.

8. The method of claim 1, wherein the set of dynamic optical parameters comprises an Area-to-Max parameter that is an integral of the dynamic optical curve with respect to time from an initial time, at which the biomarker is applied, to a time at which a maximum value of the dynamic optical curve is reached, and wherein the reference values comprise an Area-to-Max cut-off value, wherein a determined Area-to-Max value greater than the Area-to-Max cut-off value indicates a high-grade neoplasia.

9. The method of claim 8, wherein the Area-to-Max cut-off value is between about 120 calibrated units×seconds and about 170 calibrated units×seconds); and wherein the calibrated units correspond to numerical values on a 0-255 gray scale of a green channel of a color imaging system and the tissue sample initially has about an 18% reflectance.

10. The method of claim 1, wherein the set of dynamic optical parameters comprises a SlopeA parameter that is a slope of the dynamic optical curve before a maximum value of the dynamic optical curve is reached, and wherein a determined SlopeA value greater than the SlopeA cut-off value indicates a high-grade neoplasia.

11. The method of claim 1, wherein the set of dynamic optical parameters comprises a SlopeB parameter that is a slope of the dynamic optical curve after a maximum value of the dynamic optical curve is reached, and wherein a determined SlopeB value smaller than the SlopeB cut-off value indicates a high-grade neoplasia.

12. A quantitative method for determining, in vivo, tissue characteristics in a living tissue sample, comprising:
measuring, in vivo, temporal alterations of an optical property of a tissue at a plurality of spatial locations of the tissue;
calculating a dynamic optical curve from the measured optical property data for each spatial location in the plurality of spatial locations;
determining a value of a dynamic optical parameter from the dynamic optical curve for each spatial location in the plurality of spatial locations; and
determining, in vivo, numerical values expressing tissue characteristics for each spatial location in the plurality of spatial locations using a pre-determined relationship between the dynamic optical parameter value and a numerical value expressing tissue characteristics;
wherein the pre-determined relationship has been calculated using numerical values expressing tissue characteristics of a statistically significant number of reference tissue samples and wherein the numerical values were determined with quantitative pathology methods;
wherein the tissue characteristics are selected from the group consisting of: functional characteristics and structural characteristics;
wherein the tissue characteristics are related to a tissue condition;
wherein the tissue is an epithelial tissue; and
wherein the tissue condition is selected from the group consisting of: normal tissue, cervical neoplasia, HPV infection, dysplasia, pathologic, cancerous and precancerous.

13. The method of claim 12, wherein the pre-determined relationship between a dynamic optical parameter value and a numerical value expressing tissue characteristics is determined by steps comprising:
correlating a dynamic optical parameter value for a particular reference tissue sample obtained in vivo with a numerical value expressing tissue characteristics of the particular reference tissue sample, as determined by an in vitro quantitative diagnostic test, for a statistically significant number of reference tissue samples; and
determining, on the basis of said correlations, a mathematical formula relating a value of a dynamic optical parameter with a numerical value expressing tissue characteristics; wherein the mathematical formula expresses the pre-determined relationship between a dynamic optical parameter value and numerical values tissue characteristics.

14. The method of claim 12, further comprising:
generating an artificial image by correlating a color at a pixel corresponding to a spatial location with values of the dynamic optical parameters at the spatial location; wherein different colors represent different ranges of parameter value and wherein reference values of the dynamic optical parameters define limits of the ranges, thereby detecting, classifying and mapping a condition for the tissue sample, in vivo.

15. The method of claim 12, wherein the pre-determined relationship is a relationship between an 'Integral' parameter, which is an integral of a magnitude of the dynamic optical curve with respect to time over a predetermined time period, and a nuclear-to-cytoplasmic-ratio (NCR); and wherein the NCR is linearly related to the 'Integral' parameter.

16. The method of claim 12, wherein the pre-determined relationship is a relationship between a Max parameter, which is a difference between a maximum value of a magnitude of the dynamic optical curve and a value of the dynamic optical curve before the biomarker is applied, and a nuclear-to-cytoplasmic-ratio (NCR); and wherein the NCR is linearly related to the 'Max' parameter.

17. A non-transitory computer readable medium holding computer program instructions for determining a tissue condition, which when executed by a computing device causes the computing device to perform the steps of:
aligning a set of optical images obtained sequentially over a predetermined period of time from a living tissue before and after application of a biomarker; wherein the living tissue is epithelial tissue;
calculating from said aligned optical images a dynamic optical curve at a spatial location, which is a pixel or a group of pixels, on the images, the dynamic optical curve expressing temporal alterations of in optical property of the tissue provoked by application of the biomarker, for each spatial location in a plurality of spatial locations;
determining a set of dynamic optical parameters expressing the characteristics the dynamic optical curve at a spatial location, for each spatial location in the plurality of spatial locations;
comparing the dynamic optical parameter values, obtained in vivo from the tissue, with reference values including predetermined reference optical parameter value ranges and cut-off values, in a computer memory; wherein the predetermined reference optical parameter value ranges and cut-off values are known to be linked with a tissue condition; wherein the cut-off value of each dynamic optical parameter is such that the sensitivity and the specificity of the dynamic optical parameter are approximately the same; and wherein the tissue condition is selected from the group consisting of: normal tissue, cervical neoplasia, HPV infection, dysplasia, cancer and precancerous;
determining on the basis of the comparisons, a tissue condition for each spatial location in the plurality of spatial locations; and
generating an artificial image by correlating a color at a spatial location on the artificial image with values of the dynamic optical parameters calculated from the corresponding spatial location on the optical images; wherein different colors represent different ranges of parameter values and wherein reference values of the dynamic optical parameters define limits of the ranges, thereby detecting, classifying and mapping a condition for the tissue sample, in vivo.

18. The computer readable medium of claim 17, wherein the tissue is the cervix of the uterus, the optical image is diffuse reflectance image, and the biomarker is an 3%-5% acetic acid solution;

wherein the set of dynamic optical parameters comprises an 'Integral' parameter that is an integral of a magnitude of the dynamic optical curve with respect to time over a predetermined time period; and wherein the reference values comprise:

an upper 'Integral' cut-off value, wherein a determined 'Integral' value greater than the upper 'Integral' cut-off value indicates a high-grade neoplasia; and a lower 'Integral' cut-off value, wherein a determined 'Integral' value less than the lower 'Integral' cut-off value indicates an HPV infection.

19. The computer readable medium of claim 17, wherein the tissue is tissue of a cervix;

wherein the biomarker is a 3%-5% acetic acid solution;

wherein the dynamic curve is a dynamic scattering curve obtained during a time period after application of said biomarker;

wherein the set of dynamic optical parameters comprises a $T_{max}$ parameter that is a time required to reach a maximum value of the dynamic optical curve after application of the biomarker; and wherein the reference values comprise a $T_{max}$ cut-off value that is between about 80 seconds and about 100 seconds, and wherein a determined $T_{max}$ value greater than the $T_{max}$ cut-off value indicates a high-grade neoplasia.

20. The computer readable medium of claim 17, wherein the tissue is the cervix of the uterus, and the optical image is a diffuse reflectance image;

wherein the biomarker is an 3%-5% acetic acid solution; and wherein the set of dynamic optical parameters comprises an Area-to-Max parameter that is an integral of the dynamic optical curve with respect to time from an initial time, at which the biomarker is applied, to a time at which a maximum value of the dynamic optical curve is reached, and wherein the reference values comprise an Area-to-Max cut-off value, wherein a determined Area-to-Max value greater than the Area-to-Max cut-off value indicates a high-grade neoplasia.

21. A non-transitory computer readable medium holding computer program instructions for determining, in vivo, tissue characteristics in a living tissue sample, which when executed by a computing device causes the computing device to perform the steps of:

aligning a set of optical images obtained sequentially over a predetermined period of time from a living tissue sample before and after application of a biomarker; wherein the tissue sample is an epithelial tissue;

calculating from said aligned optical images a dynamic optical curve at a spatial location, which is a pixel or a group of pixels, for each spatial location in a plurality of spatial locations on the images; wherein the dynamic optical curves express temporal alterations of an optical property of the tissue at a spatial location provoked by application of the biomarker;

determining dynamic optical parameters from the dynamic optical curve at a spatial location for each of the plurality of spatial locations;

determining, in vivo, tissue characteristics at each spatial location in the plurality of spatial locations through a predetermined mathematical formula correlating the tissue characteristics with the dynamic optical parameters at each spatial location; wherein the tissue characteristics are selected from the group consisting of: microstructural tissue characteristics and functional tissue characteristics; and generating an artificial image by correlating a color at a spatial location on the artificial image with the determined tissue characteristics calculated from the corresponding spatial location on the optical images; wherein different colors represent different values for the tissue characteristics, thereby mapping tissue characteristics for the living tissue sample, in vivo.

22. The computer readable medium of claim 21, wherein said tissue is the cervix of the uterus; the optical image is diffuse reflectance image, and the biomarker is an 3%-5% acetic acid solution; and wherein the pre-determined mathematical formula linearly relates an 'Integral' parameter, which is an integral of a magnitude of the dynamic optical curve with respect to time over a predetermined time period, with a nuclear-to-cytoplasmic-ratio (NCR).

23. The computer readable medium of claim 21, wherein the tissue is a cervix of a uterus, the optical image is diffuse reflectance image, and the biomarker is an 3%-5% acetic acid solution; and wherein the pre-determined mathematical formula linearly relates a Max parameter, which is a difference between a maximum value of a magnitude of the dynamic optical curve and a value of the dynamic optical curve before the biomarker is applied, to a nuclear-to-cytoplasmic-ratio (NCR).

* * * * *